(12) United States Patent
Rondoni et al.

(10) Patent No.: US 7,715,920 B2
(45) Date of Patent: May 11, 2010

(54) TREE-BASED ELECTRICAL STIMULATOR PROGRAMMING

(75) Inventors: John C. Rondoni, Plymouth, MN (US); Martin T. Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 912 days.

(21) Appl. No.: 11/414,527

(22) Filed: Apr. 28, 2006

(65) Prior Publication Data

US 2007/0255346 A1 Nov. 1, 2007

(51) Int. Cl.
*A61N 1/18* (2006.01)
(52) U.S. Cl. .......................... 607/59; 607/2
(58) Field of Classification Search .......... 607/59
See application file for complete search history.

(56) References Cited

U.S. PATENT DOCUMENTS

| | | | |
|---|---|---|---|
| 4,236,524 A | 12/1980 | Powell et al. | |
| 4,872,122 A | 10/1989 | Altschuler et al. | |
| 4,895,574 A | 1/1990 | Rosenberg | |
| 5,005,143 A | 4/1991 | Altschuler et al. | |
| 5,240,009 A | 8/1993 | Williams | |
| 5,273,033 A * | 12/1993 | Hoffman | 607/46 |
| 5,280,792 A | 1/1994 | Leong et al. | |
| 5,358,513 A | 10/1994 | Powell, III et al. | |
| 5,383,910 A | 1/1995 | den Dulk | |
| 5,443,486 A | 8/1995 | Hrdlicka et al. | |
| 5,522,863 A | 6/1996 | Spano et al. | |
| 5,626,140 A | 5/1997 | Feldman et al. | |
| 5,645,069 A | 7/1997 | Lee | |
| 5,673,367 A | 9/1997 | Buckley | |
| 5,702,429 A | 12/1997 | King | |

(Continued)

FOREIGN PATENT DOCUMENTS

EP   0 653 224 A2   5/1995

(Continued)

OTHER PUBLICATIONS

"Notice of Transmittal of the International Search Report and the Written Opinion of the International Searching Authority, or the Declaration," dated Aug. 22, 2007 for corresponding PCT Application No. PCT/US2007/001884, (13 pgs.).

(Continued)

*Primary Examiner*—Carl H Layno
*Assistant Examiner*—Jeremiah T Kimball
(74) *Attorney, Agent, or Firm*—Shumaker & Sieffert, P.A.

(57) ABSTRACT

The disclosure describes an implantable stimulation system that guides programming with a therapeutic tree. All possible stimulation parameters are arranged on the therapeutic tree, with each level of the therapeutic tree containing a different stimulation parameter type. Each level includes nodes that are connected to nodes of adjacent levels. A user, such as a clinician or a patient, creates a program path by moving through nodes of lower levels. The stimulation parameter types are arranged so that coarse adjustments occur at higher levels of the tree and fine adjustments occur at lower levels of the tree. The nodes of the program path define the stimulation parameters of the delivered stimulation therapy. In addition, a sensor may detect a physiological function to allow the system to automatically identify therapy efficacy and create the most efficacious program path for the patient.

33 Claims, 13 Drawing Sheets

U.S. PATENT DOCUMENTS

| | | | |
|---|---|---|---|
| 5,706,403 A | 1/1998 | Shibata et al. |
| 5,713,932 A | 2/1998 | Gillberg et al. |
| 5,716,382 A | 2/1998 | Snell |
| 5,774,357 A | 6/1998 | Hoffberg et al. |
| 5,782,885 A | 7/1998 | Andersson |
| 5,810,014 A | 9/1998 | Davis et al. |
| 5,867,386 A | 2/1999 | Hoffberg et al. |
| 5,875,108 A | 2/1999 | Hoffberg et al. |
| 5,901,246 A | 5/1999 | Hoffberg et al. |
| 5,903,454 A | 5/1999 | Hoffberg et al. |
| 5,920,477 A | 7/1999 | Hoffberg et al. |
| 5,921,937 A | 7/1999 | Davis et al. |
| 5,938,688 A | 8/1999 | Schiff |
| 5,995,868 A | 11/1999 | Dorfmeister et al. |
| 5,999,854 A | 12/1999 | Deno et al. |
| 6,038,476 A | 3/2000 | Schwartz |
| 6,081,750 A | 6/2000 | Hoffberg et al. |
| 6,129,745 A | 10/2000 | Sun et al. |
| 6,171,239 B1 | 1/2001 | Humphrey |
| 6,192,273 B1 | 2/2001 | Igel et al. |
| 6,263,230 B1 | 7/2001 | Haynor et al. |
| 6,269,267 B1 | 7/2001 | Bardy et al. |
| 6,308,102 B1 | 10/2001 | Sieracki et al. |
| 6,345,200 B1 | 2/2002 | Mouchawar et al. |
| 6,370,423 B1 | 4/2002 | Guerrero et al. |
| 6,385,479 B1 | 5/2002 | Sibbitt et al. |
| 6,386,882 B1 | 5/2002 | Linberg |
| 6,400,996 B1 | 6/2002 | Hoffberg et al. |
| 6,408,290 B1 | 6/2002 | Thiesson et al. |
| 6,418,424 B1 | 7/2002 | Hoffberg et al. |
| 6,434,261 B1 | 8/2002 | Zhang et al. |
| 6,456,622 B1 | 9/2002 | Skaanning et al. |
| 6,473,653 B1 | 10/2002 | Schallhorn et al. |
| 6,480,743 B1 | 11/2002 | Kirkpatrick et al. |
| 6,480,814 B1 | 11/2002 | Levitan |
| 6,496,816 B1 | 12/2002 | Thiesson et al. |
| 6,497,655 B1 | 12/2002 | Linberg et al. |
| 6,522,928 B2 | 2/2003 | Whitehurst et al. |
| 6,530,954 B1 | 3/2003 | Eckmiller |
| 6,539,249 B1 | 3/2003 | Kadhiresan et al. |
| 6,539,263 B1 | 3/2003 | Schiff et al. |
| 6,547,746 B1 | 4/2003 | Marino |
| 6,549,804 B1 | 4/2003 | Osorio et al. |
| 6,554,762 B2 | 4/2003 | Leysieffer |
| 6,556,699 B2 | 4/2003 | Rogers et al. |
| 6,572,542 B1 | 6/2003 | Houben et al. |
| 6,575,894 B2 | 6/2003 | Leysieffer et al. |
| 6,597,943 B2 | 7/2003 | Taha et al. |
| 6,609,017 B1 | 8/2003 | Shenoy et al. |
| 6,609,032 B1 * | 8/2003 | Woods et al. ................. 607/46 |
| 6,612,983 B1 | 9/2003 | Marchal |
| 6,658,287 B1 | 12/2003 | Litt et al. |
| 6,659,968 B1 | 12/2003 | McClure |
| 6,662,051 B1 | 12/2003 | Eraker et al. |
| 6,687,538 B1 | 2/2004 | Hrdlicka et al. |
| 6,697,672 B2 | 2/2004 | Andersson |
| 6,704,595 B2 | 3/2004 | Bardy |
| 7,050,856 B2 | 5/2006 | Stypulkowski |
| 7,123,961 B1 | 10/2006 | Kroll et al. |
| 7,142,923 B2 | 11/2006 | North et al. |
| 2002/0016699 A1 | 2/2002 | Hoggart et al. |
| 2002/0038294 A1 | 3/2002 | Matsugu |
| 2002/0045804 A1 | 4/2002 | Christopherson et al. |
| 2002/0055779 A1 | 5/2002 | Andrews |
| 2002/0087201 A1 | 7/2002 | Firlik et al. |
| 2002/0091419 A1 | 7/2002 | Firlik et al. |
| 2002/0103512 A1 | 8/2002 | Echauz et al. |
| 2002/0123673 A1 | 9/2002 | Webb et al. |
| 2002/0138013 A1 | 9/2002 | Guerrero et al. |
| 2002/0151992 A1 | 10/2002 | Hoffberg et al. |
| 2003/0041866 A1 | 3/2003 | Linberg et al. |
| 2003/0043815 A1 | 3/2003 | Tinsley et al. |
| 2003/0050568 A1 | 3/2003 | Green et al. |
| 2003/0053663 A1 | 3/2003 | Chen et al. |
| 2003/0088274 A1 | 5/2003 | Gliner et al. |
| 2003/0093129 A1 | 5/2003 | Nicolelis et al. |
| 2003/0097159 A1 | 5/2003 | Schiff et al. |
| 2003/0097161 A1 | 5/2003 | Firlik et al. |
| 2003/0105409 A1 | 6/2003 | Donoghue et al. |
| 2003/0135248 A1 | 7/2003 | Stypulkowski |
| 2003/0158587 A1 | 8/2003 | Esteller et al. |
| 2003/0195569 A1 | 10/2003 | Swerdlow et al. |
| 2003/0216620 A1 | 11/2003 | Jain et al. |
| 2003/0216654 A1 | 11/2003 | Xu et al. |
| 2004/0103001 A1 | 5/2004 | Mazar et al. |
| 2004/0129271 A1 | 7/2004 | Hickle |
| 2004/0143302 A1 | 7/2004 | Sieracki et al. |
| 2004/0199217 A1 | 10/2004 | Lee et al. |
| 2004/0215288 A1 | 10/2004 | Lee et al. |
| 2004/0267330 A1 | 12/2004 | Lee et al. |
| 2005/0043774 A1 | 2/2005 | Devlin et al. |
| 2005/0060007 A1 * | 3/2005 | Goetz .......................... 607/48 |
| 2005/0060008 A1 | 3/2005 | Goetz |
| 2005/0060009 A1 | 3/2005 | Goetz |
| 2005/0060010 A1 | 3/2005 | Goetz |
| 2005/0075669 A1 | 4/2005 | King |
| 2005/0080462 A1 | 4/2005 | Jenkins et al. |
| 2005/0177206 A1 | 8/2005 | North et al. |
| 2005/0222643 A1 | 10/2005 | Heruth et al. |
| 2005/0245988 A1 | 11/2005 | Miesel |
| 2006/0020292 A1 | 1/2006 | Goetz et al. |
| 2006/0190047 A1 | 8/2006 | Gerber et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0190061 A1 | 8/2006 | Stypulkowski |
| 2006/0195145 A1 | 8/2006 | Lee et al. |
| 2006/0206162 A1 | 9/2006 | Wahlstrand et al. |
| 2006/0206163 A1 | 9/2006 | Wahlstrand et al. |
| 2006/0235472 A1 | 10/2006 | Goetz et al. |
| 2006/0259099 A1 | 11/2006 | Goetz et al. |
| 2006/0270944 A1 | 11/2006 | King |
| 2007/0265664 A1 * | 11/2007 | Gerber et al. .................. 607/2 |
| 2007/0265681 A1 * | 11/2007 | Gerber et al. ................. 607/46 |

FOREIGN PATENT DOCUMENTS

| | | | |
|---|---|---|---|
| EP | 0 541 338 B1 | 9/1996 |
| EP | 0 756 877 A2 | 2/1997 |
| EP | 0 796 636 A1 | 9/1997 |
| EP | 0 684 858 B1 | 4/1998 |
| EP | 0 848 965 A2 | 6/1998 |
| EP | 0 882 469 B1 | 9/2002 |
| EP | 0 848 965 B1 | 8/2003 |
| EP | 0 653 224 B1 | 1/2004 |
| EP | 1 192 971 B1 | 1/2005 |
| WO | WO 00/10455 A1 | 3/2000 |
| WO | WO 01/17419 A1 | 3/2001 |
| WO | WO 01/43823 A1 | 6/2001 |
| WO | WO 01/47600 A1 | 7/2001 |
| WO | WO 01/56467 A1 | 8/2001 |
| WO | WO 01/60445 A2 | 8/2001 |
| WO | WO 01/82995 A2 | 11/2001 |
| WO | WO 01/82995 A3 | 11/2001 |
| WO | WO 02/02622 A2 | 1/2002 |
| WO | WO 02/15777 A1 | 2/2002 |
| WO | WO 03/043690 A1 | 5/2003 |
| WO | WO 03/051175 A2 | 6/2003 |
| WO | WO 03/094721 A1 | 11/2003 |
| WO | WO 2004/041352 A1 | 5/2004 |
| WO | WO 2004/075982 A1 | 9/2004 |
| WO | WO 2004/096349 A1 | 11/2004 |
| WO | WO 2004/096358 A2 | 11/2004 |
| WO | WO 2005/028028 A1 | 3/2005 |

| | | |
|---|---|---|
| WO | WO 2005/039688 A2 | 5/2005 |
| WO | WO 2006/012423 A1 | 2/2006 |
| WO | WO 2006/098823 A1 | 9/2006 |
| WO | WO 2006/098824 A1 | 9/2006 |

OTHER PUBLICATIONS

Notification of Transmittal of the International Preliminary Report on Patentability dated Aug. 19, 2008 for corresponding PCT Application Serial No. PCT/US2007/001884 (12 pgs).

Office Action dated Dec. 31, 2008 for U.S. Appl. No. 11/799,114 (14 pgs.).

Responsive Amendment dated Mar. 31, 2009 for U.S. Appl. No. 11/799,114 (17 pgs.).

Office Action dated Jan. 12, 2009 for U.S. Appl. No. 11/799,113 (15 pgs.).

Responsive Amendment dated Apr. 13, 2009 for U.S. Appl. No. 11/799,113 (20 pgs.).

European Office Action dated May 29, 2009 for Application No. 07 749 160.3-1265 (2 pgs.).

Office Action dated Jul. 13, 2009 for U.S. Appl. No. 11/799,114 (14 pgs.).

Responsive Amendment dated Sep. 14, 2009 for U.S. Appl. No. 11/799,114 (17 pgs.).

Advisory Action dated Sep. 24, 2009 for U.S. Appl. No. 11/799,114 (3 pgs.).

Office Action dated Sep. 4, 2009 for U.S. Appl. No. 11/799,113 (14 pgs.).

Response dated Nov. 4, 2009 for U.S. Appl. No. 11/799,113 (11 pgs.).

\* cited by examiner

TREE-BASED ELECTRICAL STIMULATOR PROGRAMMING

TECHNICAL FIELD

The invention relates to medical devices and, more particularly, electrical stimulators.

BACKGROUND

Electrical stimulators may be used to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis. In general, an implantable stimulator delivers neurostimulation therapy in the form of electrical pulses. An implantable stimulator may deliver neurostimulation therapy via one or more leads that include electrodes located proximate to target locations associated with the brain, the spinal cord, pelvic nerves, peripheral nerves, or the stomach of a patient. Hence, stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In general, a clinician selects values for a number of programmable parameters in order to define the electrical stimulation therapy to be delivered by the implantable stimulator to a patient. For example, the clinician ordinarily selects a combination of electrodes carried by one or more implantable leads, and assigns polarities to the selected electrodes. In addition, the clinician selects an amplitude, which may be a current or voltage amplitude, a pulse width and a pulse rate for stimulation pulses to be delivered to the patient. A group of parameters, including electrode configuration (electrode combination and electrode polarity), amplitude, pulse width and pulse rate, may be referred to as a program in the sense that they drive the neurostimulation therapy to be delivered to the patient.

The process of selecting stimulation parameters can be time consuming, and may require a great deal of trial and error before a therapeutic program is discovered. The "best" program may be a program that best balances greater clinical efficacy and minimal side effects experienced by the patient. In addition, some programs may consume less power during therapy. The clinician may test stimulation parameters by manually specifying parameters based on intuition or some idiosyncratic methodology. The clinician may then record notes on the efficacy and side effects of each parameter set after delivery of stimulation via that combination. Upon receipt of patient feedback and/or observation of symptoms by the clinician, the clinician is able to compare and select from the tested programs.

SUMMARY

The disclosure is directed to techniques for guiding the programming of an electrical stimulator using a therapeutic tree and efficacy feedback. Each level of the tree includes nodes that are connected to nodes of adjacent levels, similar to a branching tree. A user, such as a clinician or a patient, creates a program path by moving through one node at each level of the tree according to efficacy feedback.

Electrical stimulation therapy is generally defined by a group of parameters, including electrode combination, electrode polarity, current or voltage amplitude, stimulation pulse width, and stimulation pulse rate. A variety of stimulation parameters are associated with the nodes in the therapeutic tree. In particular, each level of the therapeutic tree contains nodes representing adjustment of a different type of stimulation parameter.

The stimulation parameter types may be arranged so that higher priority adjustments occur at higher levels of the tree and lower priority adjustments occur at lower levels of the tree. In particular, the parameters are prioritized so that parameters believed to have the largest impact on efficacy are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

The nodes of the program path define the stimulation parameters of the delivered stimulation therapy. A clinician or patient traverses the levels and nodes of the tree based on efficacy feedback from the patient, objective efficacy observations by the clinician, and or sensed physiological conditions indicative of efficacy. The efficacy feedback permits navigation of an efficacious program path, resulting in a set of stimulation parameter values that support therapeutic efficacy.

If a selected node of the tree produces a therapeutic efficacy improvement that exceeds a threshold level, then programming proceeds down the tree to the next level of nodes connected to the selected node. If the selected node does not produce an efficacy improvement above the threshold level, then programming proceeds to other nodes at the same level of the tree as the selected node.

For example, if a selected node corresponding to a particular pulse rate change is evaluated and found to yield a sufficient efficacy improvement, the process proceeds to nodes at the next level of the tree, which may represent adjustments to a pulse width value. While adjustments to pulse width are evaluated, the pulse rate value specified by the node in the upper level is maintained. Eventually, when a suitable pulse width value improvement is found, the process may proceed to nodes in the next level of the tree to evaluate amplitude adjustments. In this case, the pulse rate and pulse width are held constant according to the selected nodes in the upper levels of the tree while different amplitudes are evaluated.

A therapeutic tree, in accordance with this disclosure, may guide a clinician, a patient, or a neurostimulator to programs containing effective parameters. A neurostimulator, for example, may communicate with a physiological sensor that provides signals indicating efficacy, or an external programmer that receives patient or clinician input. When a sensor, patient input, or clinician input indicates that involuntary bladder voiding has occurred, the neurostimulator may automatically traverse the therapeutic tree to modify the program for improved efficacy. Hence, the therapeutic tree may be used in initial programming of the neurostimulator by a clinician or patient and/or during normal operation by the neurostimulator.

In one embodiment, the disclosure provides a method for providing electrical stimulation therapy, the method comprising defining a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters, defining a program path through the tree along a series of the interconnected nodes for which efficacy of stimulation therapy delivered according to the stimulation parameters defined by the nodes exceeds a threshold level, selecting one of the nodes in the program path, and delivering the stimulation therapy to a patient based on the parameters defined by the selected node.

In another embodiment, the disclosure provides a system for providing electrical stimulation therapy, the system comprising a memory defining a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters, and a processor that defines a program path through the tree along a series of the interconnected nodes for which efficacy of stimulation therapy delivered according to the stimulation parameters defined by the nodes exceeds a threshold level, selects one of the nodes in the program path, and controls delivery of the stimulation therapy to a patient based on the parameters defined by the selected node.

In an additional embodiment, the disclosure provides A computer-readable medium comprising instructions to cause a processor to define a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters, define a program path through the tree along a series of the interconnected nodes for which efficacy of stimulation therapy delivered according to the stimulation parameters defined by the nodes exceeds a threshold level, select one of the nodes in the program path, and control delivery of the stimulation therapy to a patient based on the parameters defined by the selected node.

In various embodiments, the invention may provide one or more advantages. For example, the therapeutic tree provides a method to guide a user to find more efficacious stimulation therapy based upon patient feedback. The system also provides a system that automatically modifies stimulation therapy based on a sensor and a calculated efficacy of the therapy. In addition, the therapeutic tree may be weighted by the clinician to change how the program path is created. The patient may benefit by achieving better stimulation therapy than would be found using trial and error or other feedback mechanisms, or by achieving acceptable stimulation therapy more quickly.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
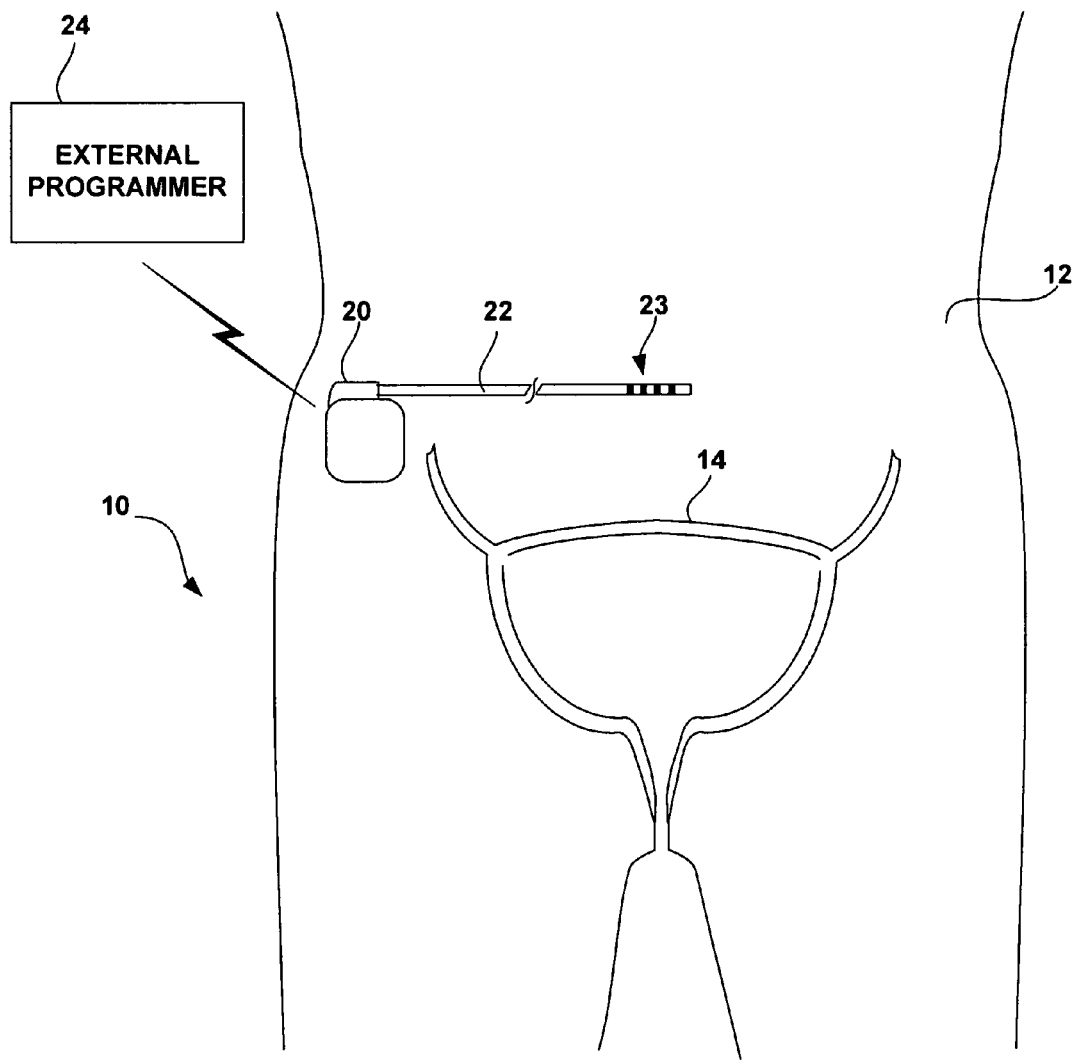
FIG. 1 is a schematic diagram illustrating an implantable stimulation system that programs stimulation based upon a therapeutic tree.

The disclosure is directed to techniques for guiding the programming of an electrical stimulator using a therapeutic tree and efficacy feedback. The techniques may be applicable to a variety of different electrical stimulators, including implantable electrical stimulators configured to deliver electrical stimulation therapy to patients to treat a variety of symptoms or conditions such as chronic pain, tremor, Parkinson's disease, epilepsy, urinary or fecal incontinence, sexual dysfunction, obesity, or gastroparesis.

The stimulator may deliver neurostimulation therapy via one or more leads that include electrodes located proximate to target locations associated with the brain, the spinal cord, pelvic nerves, peripheral nerves, or the stomach. Stimulation may be used in different therapeutic applications, such as deep brain stimulation (DBS), spinal cord stimulation (SCS), pelvic stimulation, gastric stimulation, or peripheral nerve stimulation. Stimulation also may be used for muscle stimulation, e.g., functional electrical stimulation (FES) to promote muscle movement or prevent atrophy.

In this disclosure, for purposes of illustration, the techniques for guiding programming will be described in the context of electrical stimulation therapy for urinary incontinence. Urinary incontinence, or an inability to control urinary function, is a common problem afflicting people of all ages, genders, and races. Various muscles, nerves, organs and conduits within the urinary tract cooperate to collect, store and release urine. A variety of disorders may compromise urinary tract performance and contribute to incontinence. Many of the disorders may be associated with aging, injury or illness.

In some cases, urinary incontinence can be attributed to improper sphincter function, either in the internal urinary sphincter or external urinary sphincter. For example, aging can often result in weakened sphincter muscles, which causes incontinence. Some patients also may suffer from nerve disorders that prevent proper triggering and operation of the bladder or sphincter muscles. Nerves running though the pelvic floor stimulate contractility in the sphincter. A breakdown in communication between the nervous system and the urinary sphincter can result in urinary incontinence.

Electrical stimulation of nerves in the pelvic floor may provide an effective therapy for a variety of disorders, including urinary incontinence. For example, an implantable electrical stimulator may be provided. The electrical stimulator may be a neurostimulator that delivers electrical stimulation to the sacral nerve to induce sphincter constriction and thereby close or maintain closure of the urethra at the bladder neck. In addition, electrical stimulation of the bladder wall may enhance pelvic floor muscle tone and assist fluid retention in the bladder or voiding fluid from the bladder.

An electrical stimulator may be capable of thousands of different stimulation parameter sets, or programs that define the stimulation therapy. Providing a method to program the stimulation therapy to achieve the most efficacious therapy is important to patient health and quality of life. Without an effective tool to guide a user through selecting each stimulation parameter, the patient may not benefit from an optimal therapy program. In addition, the patient may not be able to effectively modify the stimulation program during chronic therapy.

A therapeutic tree, in accordance with this disclosure, guides a user, such as a patient or physician, to create a program path when setting initial chronic stimulation parameters or modifying current stimulation programs. Stimulation parameter types, such as electrode configuration, pulse rate, pulse width, and voltage amplitude, are arranged in the therapeutic tree so that the program path that connects multiple nodes of the tree defines the stimulation.

Feedback from the patient, clinician, and/or a sensor may be used to create a program path that provides efficacious therapy for the patient. For example, if the therapeutic efficacy of stimulation delivered according to parameters associated with a selected node in the tree is increased by more than a threshold level, e.g., 50%, relative to the patient's baseline condition, the therapeutic tree will guide the user downward to nodes at the next level connected to the effective node. In this manner, the set of parameters can be refined to pursue further improvements.

Alternatively, if the efficacy improvement does not exceed the threshold, the therapeutic tree may guide the user up the tree to evaluate different nodes at the same level as the selected node. The structure of the therapeutic tree and efficacy feedback combine to decrease programming time and improve stimulation therapy efficacy, which effectively improves patient quality of life.

In this disclosure, a therapeutic tree structure and a variety of efficacy feedback media, including patient input, clinician input and sensor feedback are described for purposes of illustration. In particular, a number of specific sensor implementations are described. However, the particular sensor implementations are merely for purposes of example, and should not be considered limiting of the invention as broadly embodied and described in this disclosure.

FIG. 1 is a schematic diagram illustrating an implantable stimulation system that programs stimulation based upon a therapeutic tree. As shown in FIG. 1, system 10 includes implantable neurostimulator 20 and external programmer 24 shown in conjunction with a patient 12. Stimulation pulses are delivered to patient 12 via an electrode of lead 22, where the electrode is placed adjacent to a target tissue. In the example of FIG. 1, stimulation pulses are delivered to the target tissue to control urinary incontinence in patient 12. As mentioned above, however, the stimulator may be used with a variety of different therapies, such as deep brain stimulation, spinal cord stimulation, gastrointestinal stimulation, peripheral nerve stimulation, and the like.

With reference to FIG. 1, a user, such as a clinician or patient 12, may interact with a user interface of external programmer 24 to provide system 10 with feedback indicating the efficacy of the stimulation pulses. Based on the efficacy feedback from the user, the therapeutic tree (not shown) is used to guide programming of the stimulation therapy. In particular, the efficacy feedback directs programming through selected branches of the tree to identify a program providing desirable efficacy. The term "program" generally refers to a set of stimulation parameter, such as electrode combination, electrode polarity, voltage or current amplitude, pulse width and/or pulse rate.

Neurostimulator 20 is implanted in patient 12 at a location minimally noticeable to the patient. For pelvic floor stimulation, neurostimulator 20 may be located in the lower abdomen, lower back, or other location to secure the neurostimulator. Lead 22 is tunneled from neurostimulator 20 through tissue to reach the target tissue for stimulation delivery. At a distal tip of lead 22 are one or more electrodes 23 that transfer the stimulation pulses from the lead to the tissue. The electrodes may be paddle electrodes, circular (i.e., ring) electrodes surrounding the body of lead 22, conformable electrodes, cuff electrodes, or any other type of electrodes capable of forming unipolar, bipolar or multipolar electrode configurations.

The target tissue may be any tissue affected by electrical pulses. Such tissue includes nerves, smooth muscle, and skeletal muscle. In some embodiments, the target tissue is nerves of the pelvic floor, such as the sacral or pudendal nerves, which innervate the urinary sphincter or other muscles of the pelvic floor involved in the urinary system. The urinary sphincter aids in controlling urge and stress incontinence, and stimulation of a dysfunctional urinary sphincter may reduce or eliminate the condition of urinary incontinence.

Before stimulation begins, patient 12 may evaluate the initial condition of the patient or extent of urinary incontinence according to specific criteria associated with system 10. This baseline evaluation allows the clinician to compare the efficacy of the stimulation therapy and modify the therapy as needed. After system 10 is implanted in patient 12 and ready to deliver electrical stimulation therapy, the clinician programs neurostimulator 20 via external programmer 24. The clinician first selects an initial program that includes pre-selected stimulation parameters according to the type of stimulation needed for patient 12. In some embodiments, the clinician may manually select the initial stimulation parameters based upon previous experience or the baseline evaluation by patient 12. Patient 12 may evaluate the initial stimulation parameters before further adjustments are made. In this case, the evaluation determines how the therapeutic tree is used to guide the clinician in creating a program path for chronic stimulation therapy. If patient 12 determines that initial stimulation parameters provide an efficacy improvement greater than 50 percent, relative to the patient's baseline condition, the clinician begins to fine tune the program path by evaluating nodes in lower levels of the therapeutic tree. If the therapy efficacy improvement is less than 50 percent relative to the baseline, the clinician coarse tunes the program path by utilizing upper levels of the therapeutic tree. In other embodiments, the clinician may bypass the initial evaluation process and directly proceed to program system 10 with the therapeutic tree.

The therapeutic tree is a programming mechanism that aids the clinician and patient 12 in finding effective stimulation parameters for treating the patient. The therapeutic tree includes nodes that are associated with a stimulation parameter type and a stimulation parameter type value. The nodes are arranged in different levels of the therapeutic tree. Each node is connected to one node of a higher level and at one or more nodes of a lower level. The program path begins with a first node of a first level. If the first node is selected, the program path continues to a first node of a second level. The first node of the first level may be connected to two or more nodes of the second level. Each level contains two or more nodes. Fine tuning is used to describe moving to lower levels, e.g., the second level, the third level, and so forth. The stimulation therapy is further defined as the program path increases in the number of nodes connected by the program path. A program path can only contain one node from each level of the therapeutic tree, but the program path may be reversed to create a different program path if the stimulation therapy defined by the first program path fails to effectively treat patient 12.

Each level of the therapeutic tree contains nodes that represent one stimulation parameter type. A stimulation parameter type may include electrode configuration (combination and polarity), pulse rate, pulse width, voltage amplitude, current amplitude, stimulation duration, or any other parameter that would define electrical stimulation therapy. Therefore, the multiple nodes of each level define different values for a particular stimulation parameter type value. For example, the first level may contain electrode configuration nodes, where a first node defines one electrode configuration and a second node defines a different electrode configuration. If lead 22 contains a plurality of electrodes, the first level of the therapeutic tree may contain many nodes. As described herein, the first level is named as such because it is the first level, beyond a root level defining the patient's baseline condition that the clinician would start with when creating a program path.

Determining which stimulation parameter types are placed in what levels of the therapeutic tree, may be pre-set by the factory or a field technician before system 10 is used by the clinician or patient 12. Alternatively, the clinician may selectively associate parameter types at particular levels of the tree This association of parameter types with different levels may be viewed as a prioritization of parameter types within the tree, e.g., by selecting parameter types for upper level coarse tuning. For example, the stimulation parameter types may be arranged so that higher priority adjustments occur at higher levels of the tree and lower priority adjustments occur at lower levels of the tree. In particular, the parameters may be prioritized so that parameters believed to have the largest impact on efficacy are placed in upper levels of the tree, while parameters having lesser impacts are placed in lower levels of the tree. For example, one level of the tree may contain nodes that represent adjustments to pulse rate, while another level of the tree contains nodes that represent adjustments to pulse width, and yet another level contains nodes that represent adjustments in pulse amplitude.

In one example, the first level contains nodes specifying electrode configurations, the second level contains nodes specifying pulse rates, the third level contains nodes specifying pulse widths, and the fourth level contains nodes specifying voltage amplitudes. Hence, in this example, electrode configuration are prioritized first as having the greatest impact on efficacy, followed by pulse rate, pulse width and amplitude, all taken relative to the initial set of stimulation parameters However, more or less levels may be included in the therapeutic tree. Generally, stimulation parameter types that provide a greater change in stimulation are located near the first or second levels of the therapeutic tree, or higher in the tree, to provide coarse tuning. Parameter types that provide fine tuning are located at lower levels of the therapeutic tree. Stimulation parameter types not included in the therapeutic tree may be set to a default value by the factory or the clinician. In some embodiments, stimulation parameter types not included in the therapeutic tree may be added to the therapeutic tree if effective stimulation therapy is not defined by the stimulation parameter types originally included in the tree.

External programmer 24 may be a clinician programmer or a patient programmer. In other embodiments, external programmer 24 may be a computer connected to a network, where the programmer consults a network server to evaluate therapy efficacy and create a program path with the therapeutic tree. In the case where external programmer 24 is not connected to a network, the programmer includes the therapeutic tree in a memory such that the clinician may use the programmer to create or modify a program path at any time. If a new program path is created, the stimulation parameters, or nodes, of the new program path are transmitted to neurostimulator 20 to define the new stimulation therapy. External programmer 24 may retain all used programs in a memory so that the clinician can review the delivered therapies. In some embodiments, used and ineffective program paths may be removed from the therapeutic tree help guide the clinician and patient 12 to find an effective program path.

In other embodiments, a memory of neurostimulator 20 may store all data associated with the therapeutic tree and used program paths. External programmer 24 retrieves data from neurostimulator 20 to allow the clinician or patient 12 to create a program path. In this manner, all data is retained within patient 12 and multiple external programmers 24 may be used to treat the patient without storing private patient data away from the patient.

While the clinician or patient 12 may desire to manually create a program path for stimulation therapy, system 10 may provide automatic program path creation based upon the entered patient feedback. Depending on the efficacy of the current therapy, external programmer 24 may determine that the therapy is not "good enough" based upon certain criteria. For example, patient 12 may indicate that three incontinence events are occurring daily. If patient 12 was experiencing five incontinence events prior to therapy, external programmer 24 may determine that the therapy efficacy is not acceptable and create a new program path that has a greater chance of reducing the number of daily incontinence events. The process may continue throughout therapy to continually search for better stimulation parameters through the use of the therapeutic tree.

In cases where the therapy efficacy is very low, external programmer 24 may automatically move up several levels of the therapeutic tree to more quickly change the stimulation therapy. If the therapy is close to being very effective, external programmer 24 may only move to a different node within the same level of the tree. The therapeutic tree enables system 10 to include a feedback loop with variable instructions based upon the feedback, which may allow patient 12 to find the most efficacious therapy in a shorter amount of time.

In some embodiments, neurostimulator 20 may be used in a trial mode to evaluate the efficacy of electrical stimulation. In a trial mode, finding the most effective therapy may not be necessary to prove that stimulation therapy is effective in treating patient 12. External programmer 24 may attempt to find a program path that provides a minimal amount of therapy, e.g., a 50 percent efficacy improvement determination, and stop modifying the therapy with the therapeutic tree. In this manner, the clinician may quickly prove reasonable therapy efficacy without the risk of further modifications to the therapy that may reduce the therapy efficacy. After the trial mode is over, external programmer 24 may resume creating new program paths in the therapeutic tree when deemed necessary from the feedback of patient 12.

While the example of FIG. 1 describes stimulation therapy for treating urinary incontinence, selecting stimulation parameters though a therapeutic tree and feedback may be utilized in any number of stimulation therapies. For example, system 10 may be used in fecal incontinence, sexual dysfunction, spinal cord stimulation, lower leg pain, eating dysfunctions, deep brain stimulation, cortical brain stimulation, or any other electrical stimulation therapy.

Figure 2:
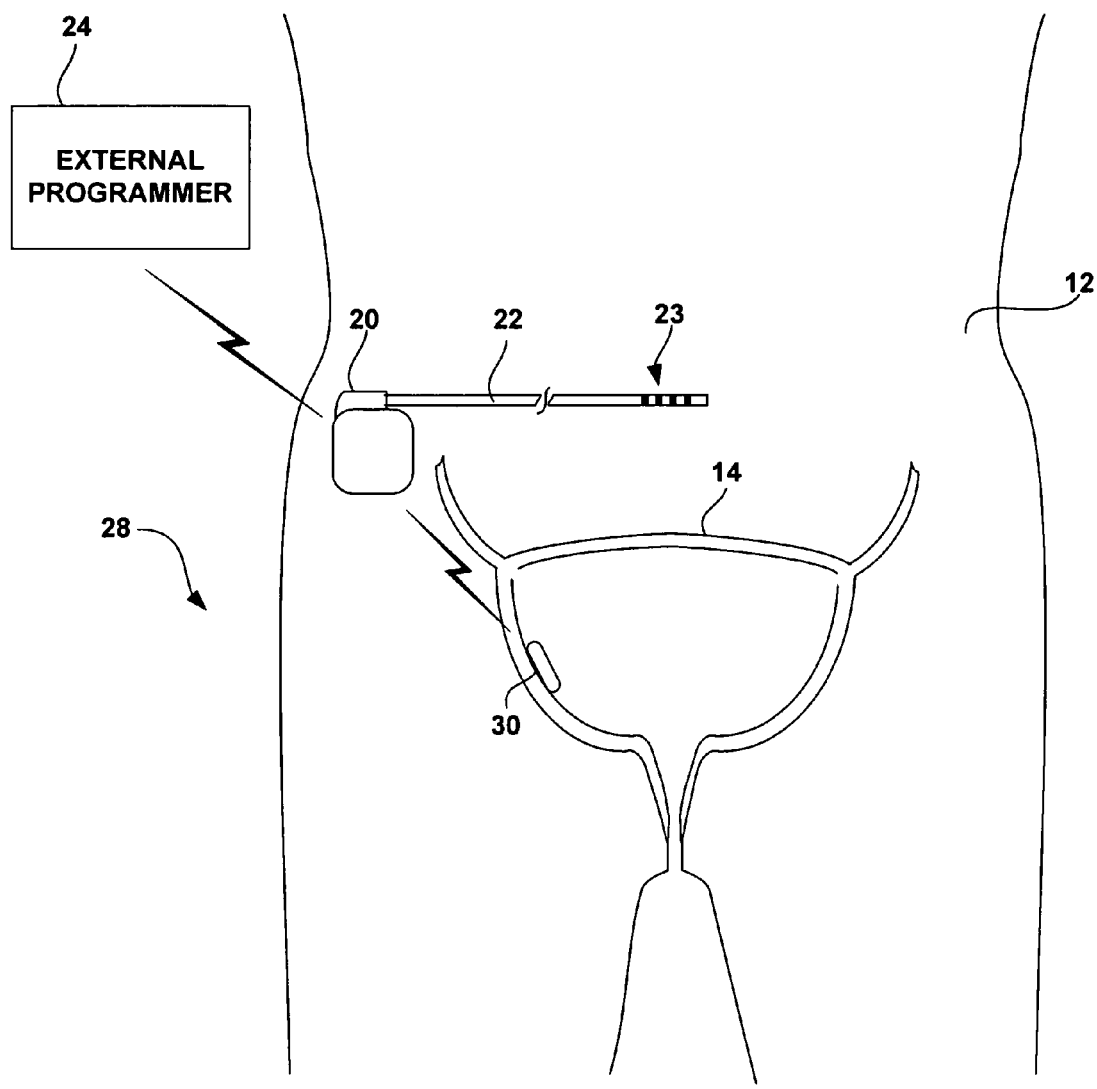
FIG. 2 is a schematic diagram illustrating an implantable stimulation system, incorporating an internal bladder sensor that senses bladder events.

FIG. 2 is a schematic diagram illustrating an implantable stimulation system, incorporating an internal bladder sensor that senses bladder events. As shown in FIG. 2, system 28 includes neurostimulator 20, external programmer 24, and sensor 30 within bladder 14. Neurostimulator 20 communicates with sensor 30 to receive information related to the physiological function of bladder 14. The physiological function information may provide an indication of therapy efficacy. Hence, one or more sensors 30 may be provided to allow neurostimulator 20 to monitor the efficacy of the stimulation therapy provided by the program path of the therapeutic tree, and create a new program path if therapy efficacy improvement is not above a predetermined threshold. Sensor 30 may also be used during initial creation of the program path, e.g., alone or in conjunction with patient and/or clinician input.

Sensor 30 may detect changes in bladder size, the bladder wall thickness, bladder pressure, urine pH, contractile force, or other characteristics of the bladder 14 that may indicate any physiological activity associated with the stimulation therapy. Sensor 30 constantly or intermittently sends data to neurostimulator 20 and/or external programmer 24. Neurostimulator 20 determines if the data from sensor 30 indicates that patient 12 is experiencing leakage or urinary voiding. Neurostimulator 20 may track any events throughout stimulation therapy. In some embodiments, sensor 30 transmits data to external programmer 24 directly or indirectly via neurostimulator 20.

While sensor 30 is implanted within patient 12, the sensor may provide information to neurostimulator 20 that indicates a voiding event has taken place without requiring the patient to enter this information into external programmer 24. Removing patient 12 from the therapy monitoring loop allows the patient to go about normal daily activities and forget about system 28.

Neurostimulator 20 may perform statistical analysis on the data received from sensor 30 to determine the probability that the data is indeed a voiding event. If a calculated confidence interval is high enough, typically greater than 95 percent, the data is identified as a voiding event and it is logged. Neurostimulator 20 may also perform a running statistical analysis on the frequency of voiding events detected by sensor 30. If a probability indicating that the current program path is not providing effective treatment is calculated, neurostimulator 20 may create a new program path in the therapeutic tree. The statistical analysis may also indicate if the program path should be fine tuned (at lower tree levels) or coarse tuned (at higher tree levels), which determines how different the new program path will be from the current program path.

In some embodiments, neurostimulator 20 gathers data from sensor 30 but does not process the data to modify stimulation therapy. When external programmer 24 communicates with neurostimulator 20, the programmer may inquire about any data collected from sensor 30. As this time, sensor 30 data may be delivered to external programmer 24 and statistical analysis performed. If necessary, external programmer 24 may create a new program path in the therapeutic tree if the efficacy is determined to be too low.

Efficacy thresholds, or the efficacy required to continue stimulation therapy, may be set by the clinician or pre-set from the factory. Generally, a 50 percent efficacy improvement relative the baseline patient condition may be required to continue using stimulation therapy, but new program paths may be created until a higher percent efficacy is reached, e.g., 80%. Once patient 12 is experiencing 80 percent efficacy, system 28 may only fine tune the program path, or change nodes of the lowest (fourth) level of the therapeutic tree. Alternatively, system 28 may not change therapy once 80 percent efficacy is reached. If less than 50 percent efficacy improvement relative to the baseline efficacy is calculated, system 28 may immediately return to the previous level of the therapeutic tree and create a new program path beginning with a different node in that level. These efficacy thresholds are only examples, and the clinician may set them to any percentage of complete efficacy or efficacy improvement, where 100 percent efficacy or efficacy improvement means there are no voiding events during therapy.

System 28 may operate very similar to system 10 (FIG. 1), without the need for direct patient feedback. Both system 28 and system 10 utilize the therapeutic tree to create new program paths and adjust stimulation therapy. In some embodiments, system 28 may wait to start a new program path until patient 12 is notified and allows the change to take place. Alternatively, system 28 may include a soft start mechanism where the new stimulation is ramped up from no stimulation, or the previous stimulation, to prevent patient 12 from being unknowingly jolted by the new stimulation therapy. Other similar safety or comfort mechanisms may also be included in system 28 when patient 12 is removed from the therapy adjustment loop.

Figure 3:
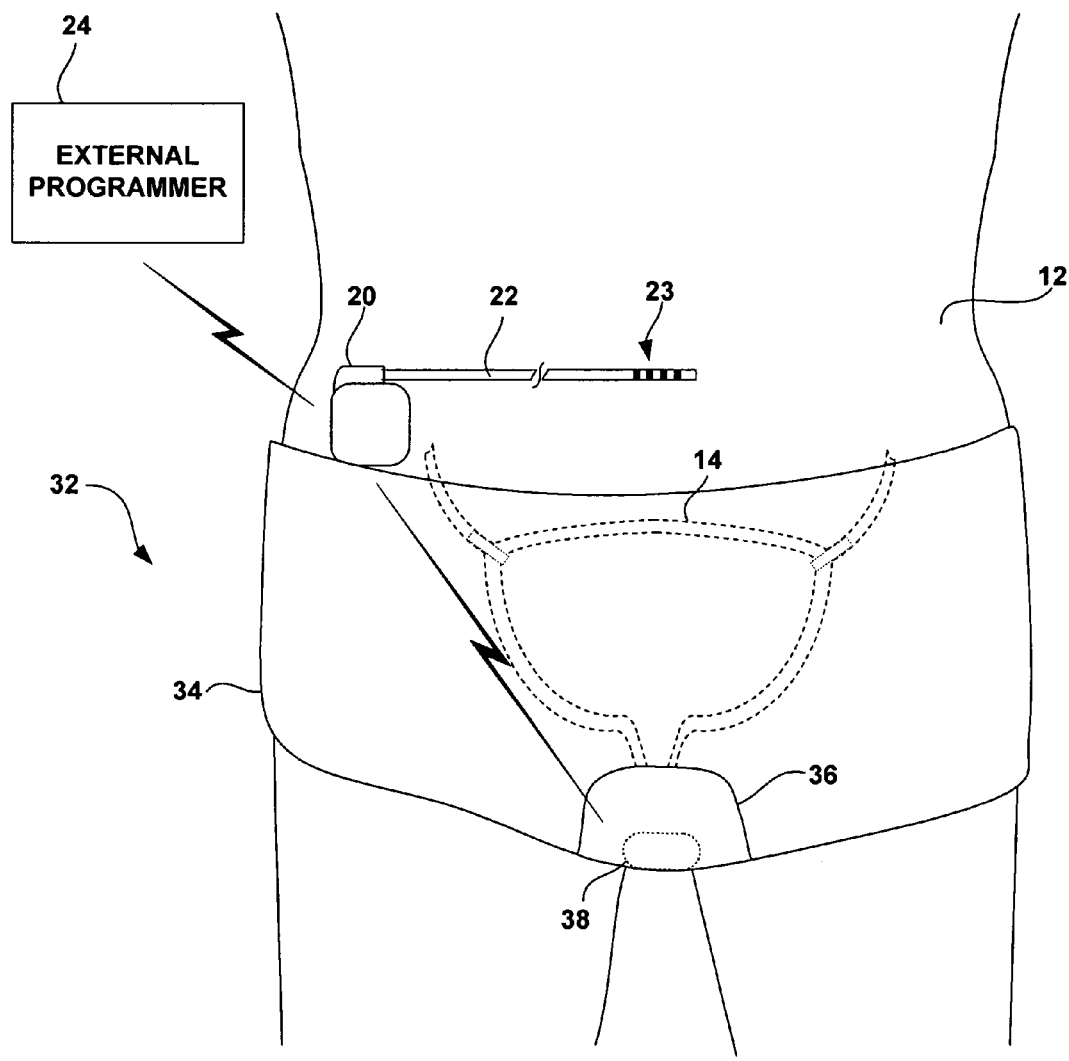
FIG. 3 is a schematic diagram illustrating an implantable stimulation system, incorporating a wearable wetting sensor that senses bladder events.

FIG. 3 is a schematic diagram illustrating an implantable stimulation system, incorporating a wearable wetting sensor that senses bladder events. System 32 is similar to system 28 of FIG. 2. in that each system includes a sensor for feedback. As shown in FIG. 3, system 32 includes stimulator 20, external programmer 24, and undergarment 34. Undergarment 34 includes pocket 36 that holds wetting sensor 38 near the opening of patient 12 urethra (not shown). Wetting sensor 38 communicates with neurostimulator 20 to create a program path that defines stimulation therapy.

Patient 12 may wear undergarment 34 under regular clothing so that wetting sensor 38 may detect voiding events. Wetting sensor 38 detects the presence of fluid which indicates that wetting has occurred. In some cases, wetting sensor 38 may be capable of also detecting fluid pH or other characteristic of the fluid to identify that the fluid is urine. Wetting sensor 38 allows system 32 to adjust stimulation therapy and create new program paths with the therapeutic tree without requiring patient 12 to have an implanted sensor provide feedback to neurostimulator 20. In some embodiments, pocket 36 may also include absorption material that absorbs voided urine, such that undergarment 34 is similar to a diaper or protective garment. In addition, undergarment 34 may be disposable, along with sensor 38.

Wetting sensor 38 may provide information to neurostimulator 20 that indicates a voiding event has taken place without requiring the patient to enter this information into external programmer 24. Removing patient 12 from the therapy monitoring loop, similar to sensor 30 of FIG. 2, allows the patient to go about normal daily activities and forget about system 32.

Neurostimulator 20 may perform statistical analysis on the data received from wetting sensor 38 to determine the probability that the data is indeed a voiding event. If a calculated confidence interval is high enough, typically greater than 95 percent, a voiding event is logged. Neurostimulator 20 may also perform a running statistical analysis on the frequency of voiding events, or amount of urine voided, detected by wetting sensor 38. If a probability is calculated that indicates that the current program path is not providing effective treatment, neurostimulator 20 may create a new program path in the therapeutic tree. The statistical analysis may also indicate if the program path should be fine tuned or coarse tuned, which determines how different the new program path will be from the current program path.

In some embodiments, neurostimulator 20 gathers data from wetting sensor 38 but does not process the data to modify stimulation therapy. As soon as external programmer 24 communicates with neurostimulator 20, the programmer may inquire about any data collected from wetting sensor 38. As this time, wetting sensor 38 data may be delivered to external programmer 24 and statistical analysis performed. If necessary, external programmer 24 may create a new program path in the therapeutic tree if the efficacy is determined to be too low.

Efficacy thresholds, or the efficacy required to continue stimulation therapy, may be set by the clinician or pre-set from the factory. Similar to system 10 or system 28, a 50 percent efficacy improvement may be required to continue using stimulation therapy, but new program paths may be created until 80 percent efficacy is reached. Once patient 12 is experiencing an 80 percent efficacy improvement, for example, system 32 may only fine tune the program path, or change nodes of the lowest (fourth) level of the therapeutic tree. Alternatively, system 32 may not change therapy once 80 percent efficacy is reached. If less than a 50 percent efficacy improvement is calculated, system 32 may immediately return to the first level of the therapeutic tree and create a new program path beginning with a second node of the first level. Again, these efficacy thresholds are only examples, any the clinician may set them to any percentage of complete efficacy.

System 32 may operate very similar to system 10 (FIG. 1), without the need for direct patient feedback. Both system 32 and system 10 utilize the therapeutic tree to create new program paths and adjust stimulation therapy. In some embodiments, system 32 may wait to start a new program path until patient 12 is notified and allows the change to take place. Alternatively, system 32 may include a soft start mechanism where the new stimulation is ramped up from no stimulation, or the previous stimulation, to prevent patient 12 from being unexpectedly jolted by the new stimulation therapy during sleep or other similarly passive activity. Other similar safety or comfort mechanisms may also be included in system 32 when patient 12 is removed from the therapy adjustment loop.

In other embodiments, any of systems 10, 28, and 32 may be restricted as to when stimulation therapy may be changed. Program path changes may occur only during a scheduled time such that patient 12 knows when the stimulation will change. For example, neurostimulator 20 may change stimulation at a certain time of the day, week or month. In addition, neurostimulator 20 may change stimulation prior to patient 12 visiting the clinic.

In any of systems 10, 28, and 34, patient 12 may have control over voltage or current amplitude without having to enter the therapeutic tree to change the program path. Since amplitude may be a fine tune stimulation parameter, it may be beneficial for patient 12 comfort to allow amplitude adjustment. In addition, each system 10, 28, and 34 may provide a therapy shut down button on external programmer 24 that immediately stops stimulation therapy.

Figure 4:
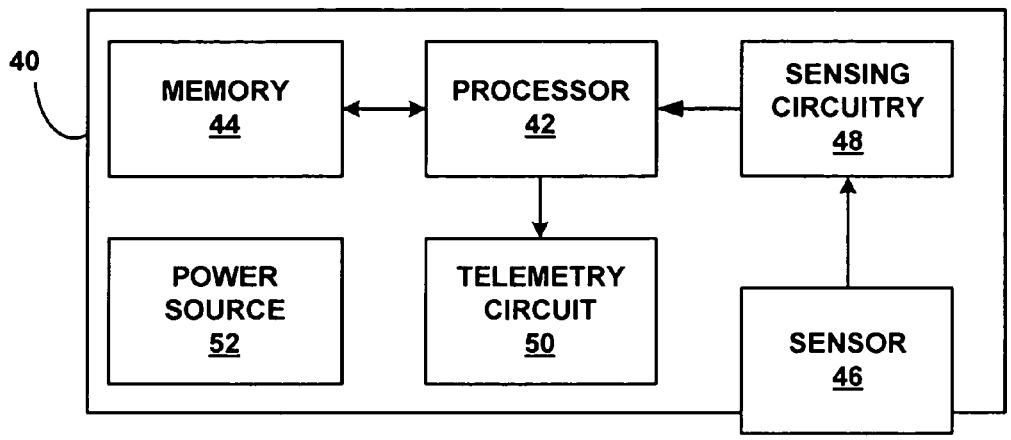
FIG. 4 is a functional block diagram illustrating various components of an exemplary implantable sensor.

FIG. 4 is a functional block diagram illustrating various components of an exemplary implantable sensor. FIG. 4 is a functional block diagram illustrating various components of an exemplary implantable bladder sensor 30 (FIG. 2) and 38 (FIG. 3), described herein as sensor 40. In the example of FIG. 4, sensor 40 includes a processor 42, memory 44, sensing circuitry 48, telemetry circuit 50, power source 52 and sensor 46. Sensing circuitry 48 may be carried on a circuit board, along with processor 42, memory 44 and telemetry circuit 50. Sensor 46 may be any sensor such as a pressure sensor, impedance sensor, ultrasound sensor, wetness sensor, pH sensor, or any other sensor that transforms mechanical information into electrical signals representative of physiological function of bladder 14. The electrical signals may be amplified, filtered, and otherwise processed as appropriate by sensing circuitry 48 within sensor 40. In some embodiments, the signals may be converted to digital values and processed by processor 42 before being saved to memory 44 or sent to neurostimulator 20 via telemetry circuitry 50.

Memory 44 stores instructions for execution by processor 42 and bladder information generated by sensing circuitry 48. Bladder data may then be sent to neurostimulator 20 or external programmer 24 for long-term storage and retrieval by a user. Memory 44 may include separate memories for storing instructions and bladder information. In addition, processor 42 and memory 44 may implement loop recorder functionality in which processor 42 overwrites the oldest contents within the memory with new data as storage limits are met, thereby conserving data storage resources within sensor 40.

Processor 42 controls telemetry circuitry 50 to send bladder information to neurostimulator 20 or external programmer 24 on a continuous basis, at periodic intervals, or upon request from the implantable stimulator or programmer. Wireless telemetry may be accomplished by radio frequency (RF) communication or proximal inductive interaction of sensor 40 with external programmer 24.

Power source 52 delivers operating power to the components of sensor 40. Power source 52 may include a small rechargeable or non-rechargeable battery and a power generation circuit to produce the operating power. Recharging may be accomplished through proximal inductive interaction between an external charger and an inductive charging coil within sensor 40. In some embodiments, power requirements may be small enough to allow sensor 40 to utilize patient motion and implement a kinetic energy-scavenging device to trickle charge a rechargeable battery. In other embodiments, traditional batteries may be used for a limited period of time. As a further alternative, an external inductive power supply could transcutaneously power sensor 40 whenever measurements are needed or desired.

Figure 5:
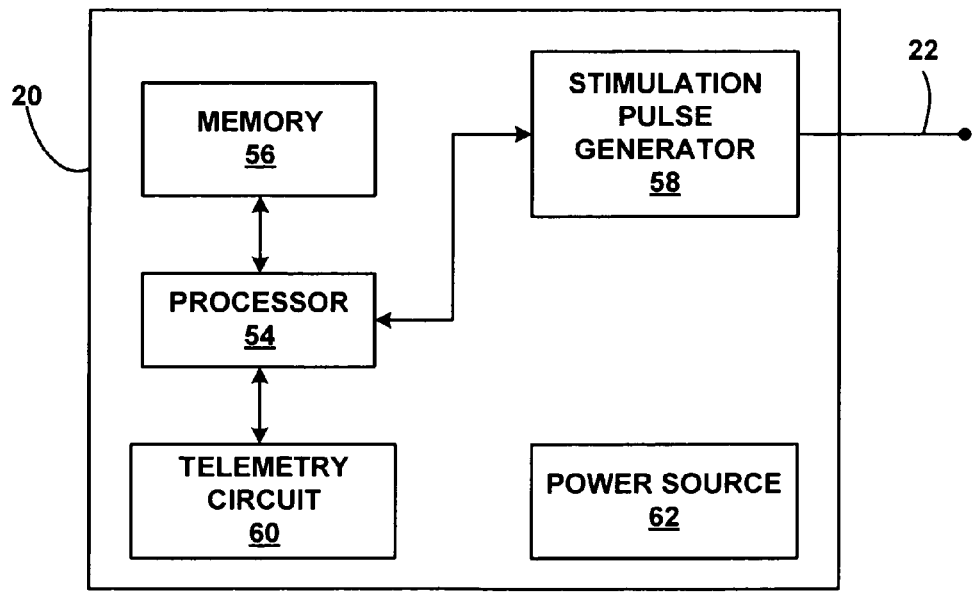
FIG. 5 is a functional block diagram illustrating various components of an implantable stimulator that communicates wirelessly with an implantable sensor.

FIG. 5 is a functional block diagram illustrating various components of an implantable stimulator that communicates wirelessly with an implantable sensor. In the example of FIG. 5, neurostimulator 20 includes a processor 54, memory 56, stimulation pulse generator 58, telemetry circuit 60, and power source 62. Memory 56 may store instructions for execution by processor 54, stimulation therapy data, and bladder information received from sensors 30 or 38 via telemetry interface. Bladder information is received from sensors 30 or 38 and may be recorded for long-term storage and retrieval by a user, and adjustment of the program path of the therapeutic tree. Memory 56 may include separate memories for storing instructions, the therapeutic tree, program path, and bladder information.

Processor 54 controls stimulation pulse generator 58 to deliver electrical stimulation therapy via one or more leads 22. Processor 54 controls telemetry circuit 60 to send and receive information. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, more preferably between approximately 5 Hz and 250 Hz, and still more preferably between approximately 10 Hz and 50 Hz.

2. Amplitude: between approximately 0.1 volts and 50 volts, more preferably between approximately 0.5 volts and 20 volts, and still more preferably between approximately 1 volt and 10 volts. In other embodiments, a current amplitude may be defined as the biological load in the voltage is delivered.

3. Pulse Width: between about 10 microseconds and 5000 microseconds, more preferably between approximately 100 microseconds and 1000 microseconds, and still more preferably between approximately 180 microseconds and 450 microseconds.

Based on bladder information received from sensors 30 or 38, processor 54 interprets the information and determines whether the program path should be changed. For example, processor 54 may perform statistical analyses of the detected bladder information to determine if the efficacy of therapy necessitates a change in the program path. Information may be received from sensors 30 or 38 on a continuous basis, at periodic intervals, or upon request from neurostimulator 20 or external programmer 24. Alternatively, or additionally, sensors 30 or 38 may transmit bladder information when there is an abrupt change in the physiological function of bladder 14, e.g., indicating contraction at the onset of involuntary leakage.

Processor 54 modifies the program path, i.e., the stimulation parameters, stored in memory 56 in response to bladder information from sensors 30 or 38, either independently or in response to programming changes from external programmer 24. Stimulation pulse generator 58 provides electrical stimulation according to the stored program path of the therapeutic tree via one or more leads 22 implanted proximate to a nerve, such as a sacral nerve. Processor 54 determines whether a new program path should be created based on the bladder information obtained form sensors 30 or 38, and/or feedback from the patient or a clinician, and loads the new program path into memory 56 for use in delivery of stimulation.

Bladder function or mechanical properties may change due to a variety of factors, such as an activity type, activity level or posture of the patient 12. Hence, for a given set of stimulation parameters, the efficacy of stimulation may vary in terms of rate of bladder expansion or contraction, due to changes in the physiological condition of the patient. For this reason, the continuous or periodic availability of bladder information from implantable sensors 30 or 38 is highly desirable.

With this bladder information, i.e., physiological function information, neurostimulator 20 is able to monitor therapy efficacy and change the program path to more effectively treat patient 12. In particular, processor 54 is able to create new program paths in order to improve pelvic floor tone or cause more effective constriction of the urinary sphincter and thereby avoid involuntary leakage. In some cases, the adjustment may be nearly instantaneous, yet prevent leakage.

As in the case of sensors 30, 38, or 40, wireless telemetry in neurostimulator 20 may be accomplished by radio frequency (RF) communication or proximal inductive interaction of neurostimulator 20 with sensors 30 or 38 or external programmer 24. Accordingly, telemetry circuit 60 may be similar to telemetry interface 50. Also, power source 62 of neurostimulator 20 may be constructed somewhat similarly to power source 52. For example, power source 62 may be a rechargeable or non-rechargeable battery, or alternatively take the form of a transcutaneous inductive power interface.

Figure 6:
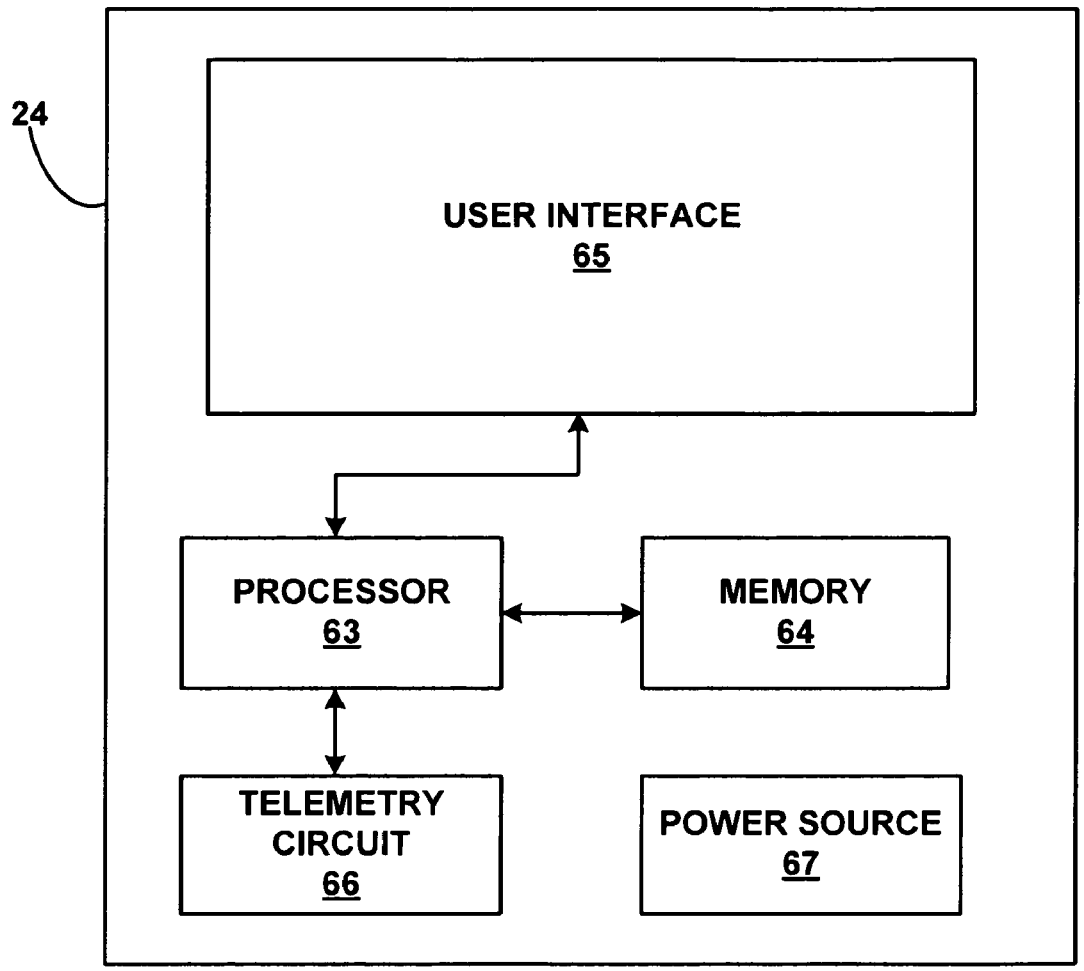
FIG. 6 is a functional block diagram illustrating various components of an external programmer that communicates wirelessly with the implantable stimulator.

FIG. 6 is a functional block diagram illustrating various components of an external programmer that communicates wirelessly with the implantable stimulator. As shown in FIG. 6, external programmer 24 includes processor 63, memory 64, telemetry circuit 66, user interface 65, and power source 67. The clinician or patient 12 interacts with user interface 65 in order to manually change the program path, adjust voltage or current amplitude, change weighting (i.e., prioritization or level) of stimulation parameter types within the therapeutic tree, or view stimulation data.

User interface may include a screen and one or more input buttons that allow external programmer 24 to receive input from a user. The screen may be a liquid crystal display (LCD), dot matrix display, or touch screen. The input buttons may include a touch pad, increase and decrease buttons, emergency shut off button, and other buttons needed to control the stimulation therapy. The clinician and patient 12 may provide therapy efficacy feedback information, such as voiding events, so that the therapeutic tree may be used to create an effective program path for the patient.

Processor 63 controls user interface 65, retrieves data from memory 64 and stores data within the memory. Processor 63 also controls the transmission of data through telemetry circuit 66 to neurostimulator 20 or sensors 30 or 38. Memory 64 includes operation instructions for processor 63 and data related to the structure of the therapeutic tree and currently chosen program path. Memory 64 may also include a history of all used program paths and voiding information.

Telemetry circuit 66 allows the transfer of data to and from neurostimulator 20, and may also communicate with sensors 30 or 38. Telemetry circuit 66 may communicate automatically with neurostimulator 20 at a scheduled time or when the telemetry circuit detects the proximity of the neurostimulator. Alternatively, telemetry circuit 66 may communicate with neurostimulator 20 when signaled by a user through user interface 65. Power source 67 may be a rechargeable battery, such as a lithium ion or nickel metal hydride battery. Other rechargeable or conventional batteries may also be used. In some cases, external programmer 24 may be used when coupled to an alternating current outlet.

Figure 7:
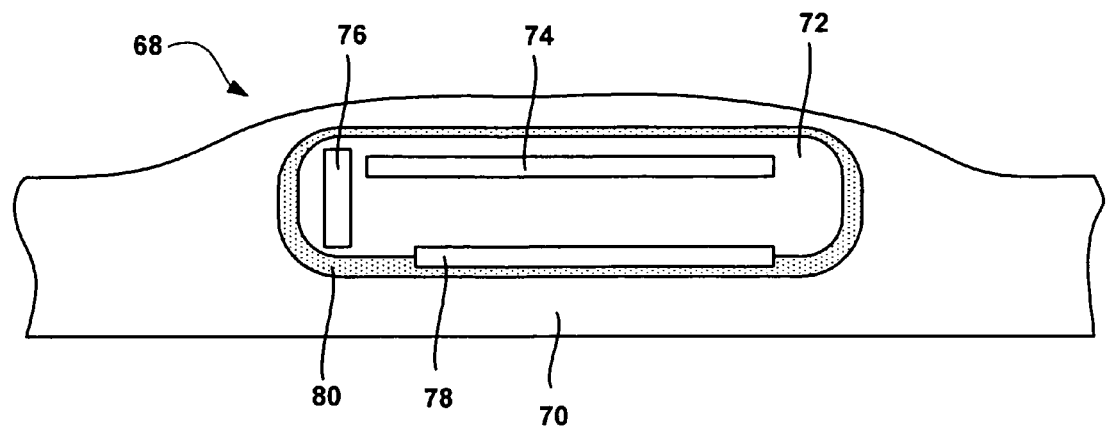
FIG. 7 is a cross-sectional side view of an implantable sensor placed within tissue of a patient.

FIG. 7 is a cross-sectional side view of an implantable sensor placed within a tissue of a patient. Sensor 68 is an embodiment of sensor 30, 38 or 40 that may be implantable in the interior or exterior of bladder 14. Sensor 68 represents one exemplary implementation of purposes of illustration, and should not be considered limiting of the invention as broadly embodied and described in this disclosure. Sensor 68 may also be housed within undergarment 34 of FIG. 3. Sensor housing 72 of sensor 68 is embedded in bladder wall 70 and includes circuit board 74, power source 76, and sensing element 78. Sensor housing 72 is in the shape of a rounded capsule and includes a smooth surface. The structure extending from housing 72 is a sensing element 78, such as a strain gauge to detect pressure or electrodes to sense electrical potentials, which slightly protrudes from the housing to sense deformation changes in bladder wall 70. Sensor 68 rests in wall cavity 80 formed within bladder wall 70. Sensor 68 may have a capsule-like shape, and may have a length of approximately 2 to 10 mm, a width of approximately 2 to 5 mm, and a thickness of approximately 1 to 5 mm. The capsule-like shape may produce a circular cross-section, in which case sensor 68 may have a diameter of approximately 1 to 5 mm, rather than width and height dimensions.

Circuit board 74, power source 76 and sensing element 78 may be similar to sensing circuitry 48, power source 52 and sensor 46 of FIG. 4. Differences between these components of each embodiment may relate to the size or shape of each component. Therefore, sensing element 78 senses a change in deformation of bladder wall 70 as bladder 14 expands and contracts. Processing electronics on circuit board 74 detect these changes sensed by sensing element 78. Circuit board 74 communicates the bladder information to neurostimulator 20, external programmer 24, or both, e.g., by wireless telemetry. Circuit board 74 also controls the operation of sensor 68.

Implanting bladder sensor 68 within bladder wall 70 may be a simple method for securing the sensor sensing element 78. As bladder 14 expands and contracts, sensing element 78 senses the changed pressure of bladder wall 70 and indicates a change in size of the bladder or an abrupt contraction. For example, a higher force in bladder wall 70 may indicate an expanding bladder 14 or a contraction. Although sensing element 78 may be a strain gauge, many other types of sensing components may be used to sense a change in deformation of bladder 14. In the case of sensor 68 being used as a wetting sensor 38, sensing element 78 may detect the presence of a fluid.

Figure 8:
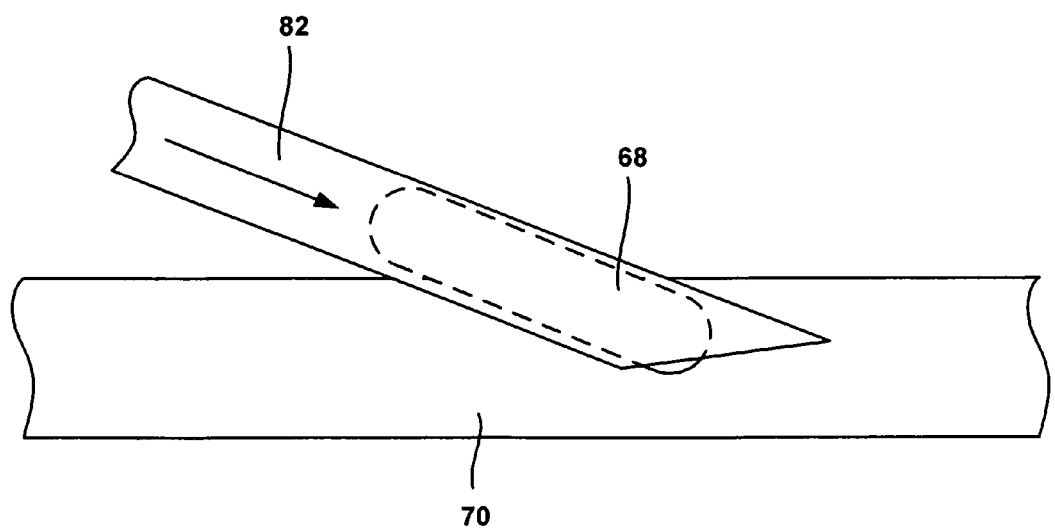
FIG. 8 is a schematic diagram illustrating endoscopic deployment of the implantable sensor of FIG. 7.

FIG. 8 is a schematic diagram illustrating endoscopic deployment of the implantable sensor of FIG. 7. Bladder sensor 68 may be implanted through endoscopic, laparoscopic, or similar minimally invasive techniques. A surgeon makes a few small incisions in the abdomen of patient 12 and guides bladder sensor 68 within needle 82 to bladder 14 with the aid of a small camera. Needle 82 may be constructed of a metal alloy and comprise a hollow cylinder and a pointed distal end for puncturing bladder wall 70. Needle 82 includes bladder sensor 68 and a fluid to force the sensor out of the needle. An exemplary fluid may be saline or other biocompatible fluid. In other embodiments, needle 82 may comprise a catheter or other hollow delivery vehicle.

Once needle 82 in positioned at the appropriate location of bladder 14, the surgeon may force sensor 68 into place. Removing needle 82 from bladder wall 70 allows the external tissue of bladder wall 70 to close and surround sensor 68. In some embodiments, the surgeon may suture the insertion hole of bladder wall 70 to promote tissue healing. The suture may comprise resorbable or non-resorbable suture or staples. When implanting sensor 68, the inner surface of bladder wall 70 should not be breached in order to prevent patient 12 from developing infection or other health problems.

In other embodiments, bladder sensor 68 may be implanted through more invasive procedures, such as open abdominal surgery which exposes bladder 14. In some embodiments, multiple sensors 70 may be placed around bladder 14 to generate an average expansion or contraction of the entire bladder.

Bladder sensor 68 has a biocompatible housing, which may be formed from titanium, stainless steel or other materials. In some embodiments, bladder sensor 68 may carry one or more expandable elements that help to anchor the sensor within the bladder wall. The expandable elements may be constructed from a hydrogel material. During implantation, the expandable elements are in a dehydrated state, in which the expandable elements are smaller. But when implanted in the body of a patient, the expandable elements absorb water from the body tissues and assume a hydrated state. In the hydrated state, the expandable elements have a larger perimeter. Expansion of the expandable elements resists migration of the sensor 68 within bladder wall 70.

Figure 9:
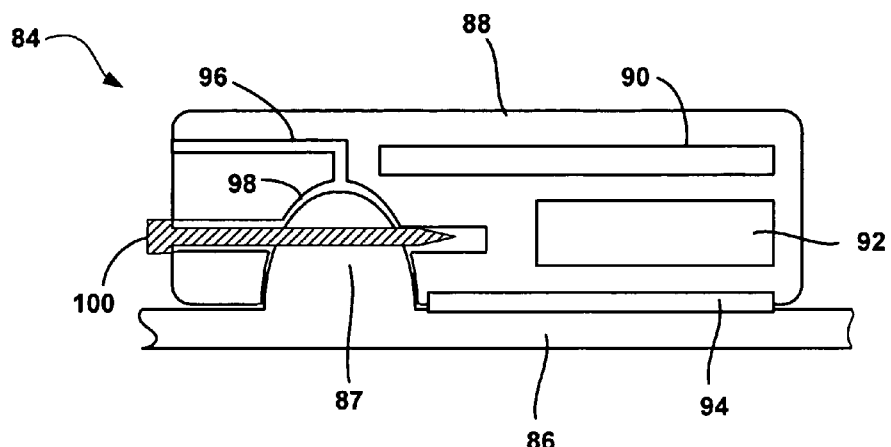
FIG. 9 is a cross-sectional side view of an implantable sensor attached to tissue of a patient.

FIG. 9 is a cross-sectional side view of an implantable sensor attached to a tissue of a patient. Sensor 84 is an embodiment of sensor 30, which is attachable within patient 12. As shown in FIG. 9, sensor 84 includes a sensor housing 88 and sensing element 94 that extends from the housing. Sensing element 94 may be a strain gauge sensor that senses mechanical deformation of the wall of bladder 14. Sensing element 94 may be coupled to a circuit board 90 within sensor 84. A power source 92, such as a battery, may be provided to power circuit board 90, sensing element 94 or both. Circuit board 90 includes processing electronics to process signals generated by sensing element 94, and generate bladder information based on the signals. In addition, circuit board 90 may include telemetry circuitry for wireless telemetry with neurostimulator 20, external programmer 24, or both. Sensor 84 is attached to bladder wall 86 by fastening pin 100 through tissue 87. Vacuum channel 96 applies negative pressure in vacuum cavity 98 to draw in a portion of bladder wall 86, i.e., tissue 87.

Power source 92 may take the form of a small rechargeable or non-rechargeable battery, which may be configured as a coin cell or pin cell. Different types of batteries or different battery sizes may be used, depending on the requirements of a given application. To promote longevity, power source 92 may be rechargeable via induction or ultrasonic energy transmission, and includes an appropriate circuit for recovering transcutaneously received energy. For example, power source 92 may include a secondary coil and a rectifier circuit for inductive energy transfer. Power generation or charging electronics may be carried on circuit board 90. In still other embodiments, power source 92 may not include any storage element, and sensor 84 may be fully powered via transcutaneous inductive energy transfer. As a further alternative, neurostimulator 20 or programmer 24 may be configured to apply inductive power to sensor 84 whenever sensing is desired. In this case, when inductive power is not applied, sensor 84 is asleep. Upon application of inductive power, sensor 84 wakes up, acquires a sense signal, and transmits the signal to programmer 24 or neurostimulator 20. Accordingly, neurostimulator 20 or programmer 24 determines the sampling rate of sensor 84 by powering up the sensor at desired intervals.

In the exemplary embodiment of FIG. 9, sensor 84 includes a strain gauge as sensing element 94 to sense mechanical deformation of the wall of bladder 14 and thereby indicate changes in bladder 14 size or shape or sense contractions. Sensing element 94 senses the stretch of bladder 14 to detect the expansion and contraction, or increase and decrease, in size of bladder 14, and thereby senses if voiding has occurred. The expansion and contraction may be monitored as gradual or instantaneous changes. For example, gradual expansion may indicate a gradual filling of bladder 14, while a rapid or instantaneous change may indicate a bladder muscle contraction and the possibility of imminent, involuntary voiding.

The disclosure is not limited to the use of a strain gauge for sensing or detecting changes in the size, wall thickness, shape or volume of bladder 14. For example, other embodiments may include one or more electrodes for sensing the electrical activity of the muscles surrounding bladder 14. Detecting muscle activity may be correlated with changes in bladder size or contraction. In other embodiments, sensor 84 may utilize an ultrasound transducer to sense the thickness of the wall of bladder 14 or the distance to the opposite wall of bladder 14. Further, sensor 84 may contain more than one sensing component, such as two strain gauges. In each case, sensor 84 is deployed on or within an exterior wall of bladder 14.

Strain gauge sensing element 94 may be formed with a flexible material, including polyurethane or silicone. In other embodiments, the strain gauge may be formed with a flexible polymer or metal alloy. The strain gauge may be able to sense small changes in bladder 14 wall stretch or deformation for detection of voiding events. The strain gauge may carry a circuit containing resistive elements, which may be printed, deposited or otherwise formed on the flexible material. In some embodiments, the strain gauge may include small protrusions or adhesion points with stick to certain locations on bladder wall 86. As bladder wall 86 expands or contracts, these locations will move with respect to each other.

Strain gauge sensing element 94 senses the movement of bladder wall 86 in terms of changes in impedance, voltage, or other electrical characteristics of the circuit formed on the strain gauge to sense the expansion or contraction of bladder 14. Processing electronics carried by circuit board 90, or carried by neurostimulator 20 or external programmer, process the sensed bladder condition or activity signal to detect expansion or contraction of the bladder 14. In particular, the signal output by sensing element 94 can be used to sense a urine fill stage of bladder 14, which may be indicative of progression toward a voiding event, or a muscle contraction, which may be indicative of an imminent voiding event.

The electrical characteristics may be monitored for rapid or instantaneous changes indicative of bladder contraction, as well as slow, gradual changes indicative of bladder filling. Rapid and gradual changes may both indicate progression of the bladder toward an imminent voiding event. For example, contraction may result in an immediate leakage of urine, while bladder filling may result in an eventual leakage of urine when the bladder becomes too full. In both cases, the events are logged to provide feedback to neurostimulator 20. The characteristics measured by sensing element 94 and processing electronics carried by circuit board 90 may be sent to neurostimulator 20 or programmer 24 as raw measurements or as bladder condition or activity signals indicating a bladder condition, such as a voiding state.

Sensor housing 88 may be made from a biocompatible material such as titanium, stainless steel or nitinol, or a polymeric material such as silicone or polyurethane. Another material for fabrication of sensor housing 88 is a two-part epoxy. An example of a suitable epoxy is a two-part medical implant epoxy manufactured by Epoxy Technology, Inc., mixed in a ratio of 10 grams of resin to one gram of activator. In general, sensor housing 88 contains no external openings, with the exception of the opening containing sensing element 94, thereby protecting power source 92 and circuit board 90 from the environment within bladder 14. The opening in sensor housing 88 that receives sensing element 94 is sealed to prevent exposure of interior components.

In some embodiments, sensor housing 88 may have a capsule-like shape with a length in a range of approximately 2 to 15 mm, a width in a range of approximately 2 to 10 mm, and a height in a range of approximately 2 to 10 mm. The capsule-like shape may produce a circular cross-section, in which case sensor housing 88 may have a diameter of approximately 3 to 10 mm, rather than width and height dimensions. Vacuum cavity 98 may be sized to capture a volume of bladder wall tissue on the order of approximately 1 to 5 mm$^3$.

Inward deflection of sensing element 94 may signal the expansion of bladder 14. This expansion may be due to the gradual addition of urine in the bladder or a contraction of muscle in bladder wall 86. During expansion of bladder 14, neurostimulator 20 may provide electrical stimulation to enhance pelvic floor tone or urinary sphincter function, for example, to keep urine within the bladder. Once sensing element 94 indicates a sufficiently large expansion, electronics on circuit board 90 generate bladder information based on the expansion. Sensor 84 may communicate the information directly to external programmer 24 or neurostimulator 20 by wireless telemetry. In other embodiments, sensor 84 may be coupled to implantable neurostimulator 20 by a wired connection.

Adjustment of the program path stored in neurostimulator 20 may be responsive to bladder information transmitted by implantable sensor 84. For example, if voiding events are happening at a rate greater than acceptable for therapy, neurostimulator 20 may alter the program path of the therapeutic tree to create a new program path and adjust stimulation therapy to a more effective therapy. Sensor 84 may transmit bladder information substantially continuously or periodically, e.g., every few seconds or minutes. In some embodiments, sensor 84 may transmit bladder information when there is an abrupt change sensed by sensing element 94, e.g., a deformational change that exceeds a predetermined threshold, indicating a contraction.

Attaching implantable sensor 84 to the bladder wall 86 of bladder 14 may be accomplished in a variety of ways, but preferably is completed in a manner that will not excessively injure bladder 14 or otherwise cause excessive trauma during implantation. Preferably, attachment should cause limited inflammation and substantially no adverse physiological modification, such as tissue infection or a loss in structural integrity of bladder 14. However, it is desirable that implantable sensor 84 also be attached securely to the attachment site in order to provide an extended period of measurement without prematurely loosening or detaching from the intended location.

As an example, sensor housing 88 may contain a vacuum cavity 98 that permits a vacuum to be drawn by a vacuum channel 96. The vacuum is created by a deployment device having a vacuum line in communication with vacuum channel 96. The vacuum draws tissue 87 from bladder wall 86 into vacuum cavity 98. Once tissue 87 of bladder wall 86 is captured within vacuum cavity 98, a fastening pin 100 is driven into the captured tissue to attach sensor housing 88 within bladder 14. Fastening pin 100 may be made from, for example, stainless steel, titanium, nitinol, or a high density polymer.

The shaft of pin 100 may be smooth or rough, and the tip may have a sharp point to allow for easy penetration into tissue. Fastening pin 100 may be driven into housing 88 and tissue 87 of bladder wall 86 under pressure, or upon actuation by a push rod, administered by a deployment device. In another embodiment, implantable sensor 84 may be attached without the use of a penetrating rod but with a spring-loaded clip to pinch trapped bladder wall 86 within cavity 98. A variety of other attachment mechanisms, such as pins, clips, barbs, sutures, helical screws, surgical adhesives, and the like may be used to attach sensor housing 88 to bladder wall 86 of bladder 14.

In the example of FIG. 2, sensor housing 88 of implantable sensor 84 is attached to the interior wall of bladder 14. However, the attachment site for sensor housing 88 could be at any position on bladder wall 86 that does not interfere with bladder function or other organ function. For example, sensor housing 88 may be placed in the top of the bladder or near the urethra. In some patients, the most desirable position may coincide with the least invasive implantation surgery. Sensor 84 may be surgically implanted using open surgery or laparoscopic techniques.

Figure 10:
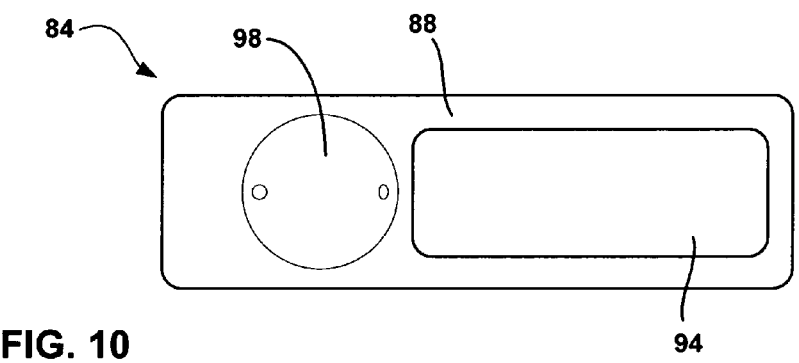
FIG. 10 is a bottom view of the implantable sensor of FIG. 9.

FIG. 10 is a bottom view of the implantable sensor of FIG. 9. Sensor housing 88 includes sensing element 94 and vacuum cavity 98, which come into contact with bladder wall 86. While sensing element 94 is rectangular and large with respect to sensor housing 88 to contact a large surface area of bladder wall 86, some embodiments may include two or more sensing elements, such as strain gauges of similar or different shapes. For example, housing 88 may include a sensing element on each end of housing 88 separated by vacuum cavity 98.

Vacuum cavity 98 holds a portion of tissue from bladder wall 86 in order to keep sensing element 94 in contact with the exterior surface of bladder 14. In some embodiments, sensor housing 88 may contain more than one vacuum cavity to attach to multiple points along bladder wall 86. For example, one vacuum cavity on each end of housing 88 may provide secure contact between sensing element 94 and bladder wall 86. In other embodiments, housing 88 may be formed into a different shape than a rectangle. For example, housing 88 may comprise a circular shape or concave shape to better fit the curvature of bladder 14.

Figure 11:
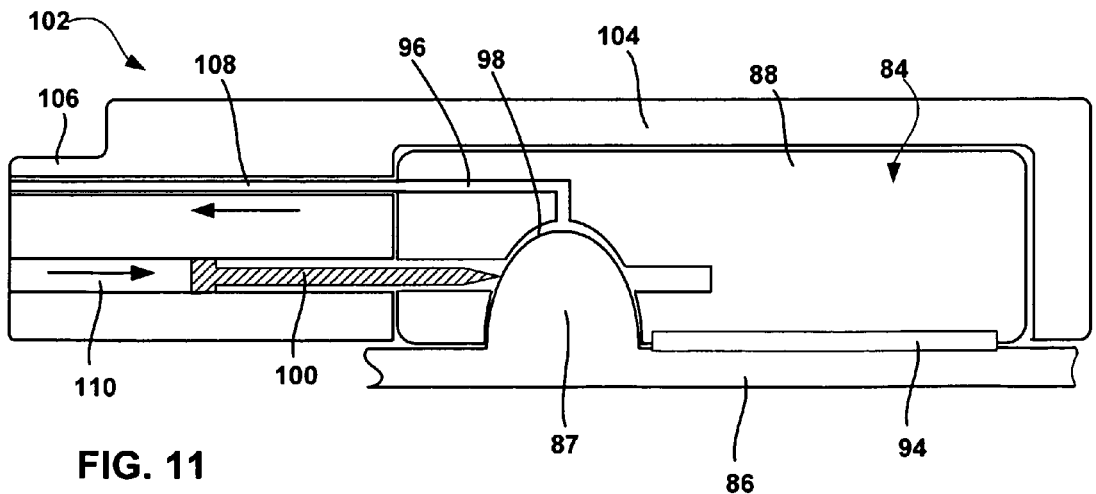
FIG. 11 is a cross-sectional side view of a deployment device during deployment and fixation of the implantable sensor of FIG. 9

FIG. 11 is a cross-sectional side view of a deployment device during deployment and fixation of the implantable sensor of FIG. 9. In the example of FIG. 11, deployment device 102 includes a distal head 104. Distal head 104 may be mounted on an elongated sheath 106 (partially shown in FIG. 11) configured for laparoscopic introduction into patient 12 through a trocar. Deployment device 102 may be used with other laparoscopic components, such as a gas distension tube for inflating the pelvic cavity to facilitate access to bladder 14, and a visualization scope for viewing the implantation site. In some embodiments, visualization components may be integrated with deployment device 102.

As shown in FIG. 11, distal head 104 receives a vacuum line 108 and a positive pressure line 110 via elongated sheath 106. Vacuum line 108 is coupled to a vacuum outside of patient 12 via a tube or lumen extending along the length of deployment device 102. Similarly, positive pressure line 110 is coupled to a positive pressure source (not shown) via a tube or lumen extending along the length of deployment device 102. Vacuum line 108 is in fluid communication with vacuum channel 96 and vacuum cavity 98, and permits the physician to draw a vacuum and thereby capture tissue 87 of bladder wall 86 within the vacuum cavity. Positive pressure line 110 permits the physician to apply a pulse of high pressure fluid, such as a liquid or a gas, to drive fixation pin 100 into sensor housing 88 and through tissue 87 of bladder wall 86. Pin 100 thereby fixes sensor housing 88 to external bladder wall 86. In some embodiments, a membrane mounted over an opening of positive pressure line 110 may be punctured by pin 100.

Once fixation pin 100 attaches sensor 84 to bladder 14, vacuum line 108 is no longer needed. However, in some embodiments, vacuum line 108 may be used to detach pressure sensor 84 from distal head 104 of deployment device 102. By terminating vacuum pressure, or briefly applying positive pressure through vacuum line 108, for example, head 104 may separate from sensor 84 due to the force of the air pressure. In this manner, vacuum line 108 may aid in detachment of sensor 84 prior to removal of deployment device 102.

As described previously in FIG. 9, fixation pin 100 punctures bladder wall 86 for fixation of sensor 84. While the force of this fixation may vary with patient 12, deployment device 102 provides adequate force for delivery of pin 100. In an exemplary embodiment, positive pressure line 110 is completely sealed and filled with a biocompatible fluid (such as water, saline solution or air). Sealing the end of positive pressure line 110 is fixation pin 100 or a head on fixation pin 100.

Fixation pin 100 is generally able to move within positive pressure line 110 much like a piston. Force to push fixation pin 100 through tissue 87 of bladder wall 86 captured in vacuum cavity 98 is created by application of a pulse of increased fluid pressure within positive pressure line 110. For example, the physician may control a positive pressure source via control handle attached to deployment device 102. This simple delivery method may provide high levels of force, allow multiple curves and bends in deployment device 102, and enable a positive pressure line 110 of many shapes and sizes.

In an alternative embodiment, a flexible, but generally incompressible, wire may be placed within positive pressure line 110 and used as a push rod to force fixation pin 100 through the captured tissue 87 of bladder wall 86. This wire presents compressive force from the control handle of deployment device 102 directly to fixation pin 100. This method may eliminate any safety risk of pressurized fluids entering patient 12 or, in some embodiments, permit retraction of pin 100 after an unsuccessful fixation attempt. If attached, the flexible wire may be attached to pin 100 and pulled back to remove the pin from tissue 87. The flexible wire may be sheared from fixation pin 100 for detachment purposes as distal head 104 releases sensor 84. This detachment may be facilitated by a shearing element or low shear stress of the wire.

In FIG. 11, deployment device 102 illustrates the attachment of vacuum line 108 and positive pressure line 110 to one end of sensor 84. In some embodiments, deployment device 102 may attach vacuum line 108 and positive pressure line 110 to their respective channels opening on the top of sensor housing 88 instead of the side of sensor housing 88. This change in location may facilitate attachment of sensor 84 from a variety of locations or on certain locations on the outside of bladder 14.

Deployment device 102 is introduced to patient 12 by a small incision in the abdomen of the patient. A surgeon may guide distal head 104 through the abdominal space to the exterior of bladder 14. Once at bladder 14, the surgeon locates the desired spot for attaching sensor 84. Sensor 84 is then pressed up against bladder wall 86 and the vacuum is initiated to bring tissue 87 into vacuum cavity 98 before fixation pin 100 is driven through tissue 87. Deployment device releases sensor 84 and is removed from patient 12.

In other embodiments, sensor 84 may be attached to bladder 14 through open abdominal surgery to precisely locate the attachment point on bladder 14. In this type of procedure, deployment device 102 may or may not be used to attach sensor 84 to bladder wall 86. In some embodiments, deployment device 102 may include a small endoscopic camera in the distal head 104. The camera may enable the physician to better guide deployment device 102 through a small opening in patient 12 to a desired attachment location on the external surface of bladder 14 in less time with more accuracy, as is common in endoscopic surgery. Images may be displayed using video fed to a display monitor.

Distal head 104 may be disposable. Disposable devices that come into contact with patient 12 tissues and fluids greatly decrease the possibility of infection in implantable devices. In other embodiments, the entire deployment device 102 may be manufactured from robust materials intended for multiple uses. The device would then need to be sterilizable between uses. In still a further embodiment, the features of distal head 104 may be incorporated into sensor 84. In this configuration, sensor 84 may be larger in size but would include the necessary elements for attachment within the device. After attachment, the entire sensor would detach from the handle of deployment device 102, reducing the difficulty of removing the entire deployment device 102, including distal head 104.

After the useful life of implantable sensor 84 is complete or it is no longer needed within patient 12, it can be removed from patient 12 in some manner. Alternatively, sensor 84 may simply remain in place. As an example, deployment device 102 may be reinserted into patient 12, navigated to bladder 14, and reattached to sensor 84. Deployment device 102 may then be withdrawn from bladder 14, explanting sensor 84 from patient 18. Alternatively, a surgeon may perform open abdominal surgery to remove the implanted sensor 84 and neurostimulator 20.

Figure 12:
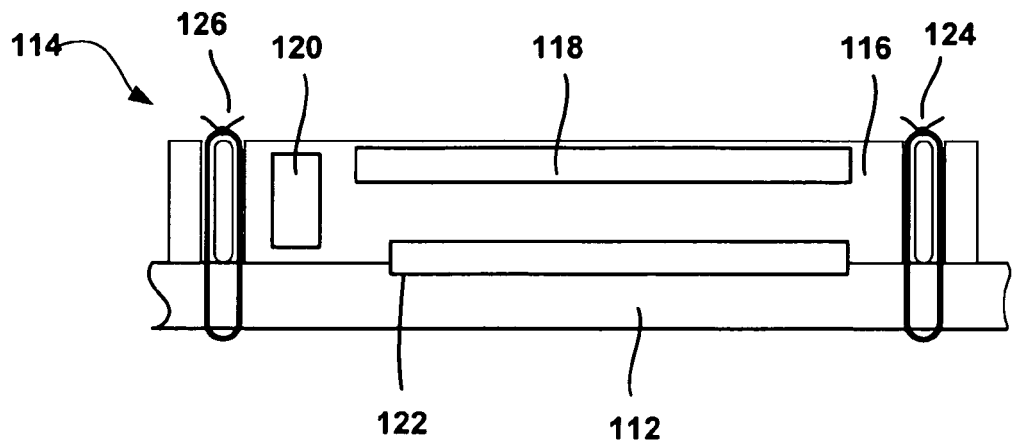
FIG. 12 is an enlarged schematic diagram illustrating an implantable sensor sutured to a tissue of a patient.

FIG. 12 is an enlarged schematic diagram illustrating an implantable sensor sutured to a tissue of a patient. As shown in FIG. 12, sensor 114 is an embodiment of sensors 30 or 38. In the case of sensor 30, sensor 114 is sutured to bladder 14. In the case of sensor 38, sensor 114 is sewn to pocket 36 of undergarment 34. Sensor housing 116 is attached to bladder wall 112 and includes circuit board 118, power source 120, and sensing element 56. Sutures 124 and 126 are used to attach bladder sensor 114 to bladder wall 112. Although only two sets of sutures can be shown in FIG. 5, sensor 114 may include four or more sets, one at each corner of the rectangular shaped sensor.

Circuit board 118, power source 120 and sensing element 122 may all be similar to circuit board 90, power source 92 and strain gauge 94 of FIG. 9. In addition, sensor housing 116 may be functionally similar to sensor housing 88 of FIG. 9. Differences between these components of each embodiment may relate to only the size or shape of each component. As in some embodiments of sensing element 94, sensing element 122 may include a strain gauge sensor that senses a change in deformation of bladder wall 112 as bladder 14 expands and contracts. Sensing element 122 sends the bladder information to circuit board 118. Circuit board 118 wirelessly communicates the bladder information to neurostimulator 20, external programmer 24, or both. Circuit board 118 also may control the operation of sensor 114.

Bladder sensor 114 may be implanted through laparoscopic techniques, similar to sensors 30 or 38. For example, a surgeon may make a few small incisions in the abdomen of patient 12 and guide bladder sensor 114 to bladder 14 with the aid of a small camera. Once sensor 114 is placed on the external surface bladder wall 112, the surgeon uses sutures to tie sensor 114 to bladder wall 112, which is illustrated by sutures 124 and 126 in FIG. 12. The sutures may or may not penetrate through bladder wall 112, and no urine will escape bladder 14 in either case.

In other embodiments, bladder sensor 114 may be implanted through more invasive procedures, such as open abdominal surgery which exposes bladder 14. In some embodiments, metal or plastic staples may be used to fix sensor 16 to bladder wall 112 instead of nylon sutures. In some embodiments, multiple sensors 114 may be placed around bladder 14 to generate an average expansion or contraction of the entire bladder.

Once attached to bladder wall 112, sensing element 122 may be securely forced against bladder wall 112. As bladder 14 expands and contracts, sensing element 122 may sense the changed pressure by bladder wall 112 and indicate a change in size of the bladder. Similar to sensing element 94 of FIG. 9, many other types of sensing components may be used to sense a change in deformation of bladder 14. However, a strain gauge is described herein for purposes of illustration.

Figure 13:
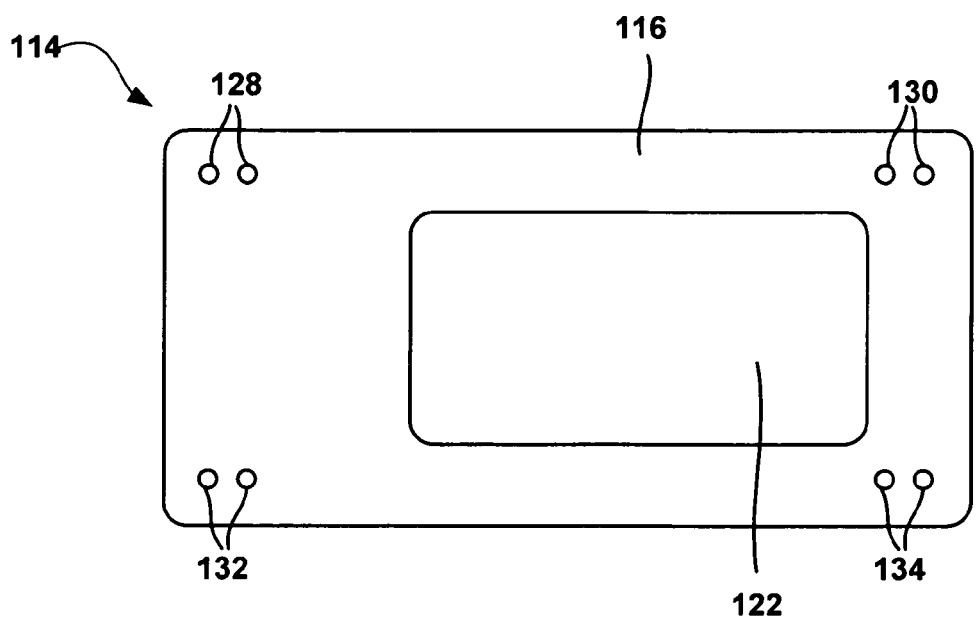
FIG. 13 is an enlarged, bottom view of the implantable sensor of FIG. 12.

FIG. 13 is an enlarged, bottom view of the implantable sensor of FIG. 12. Bladder sensor 114 includes sensor housing 116 and sensing element 122. Fixation holes 128, 130, 132 and 134 are voids in housing 116 and allow suture to be passed through housing 116 in order for sensor 114 to be attached to bladder wall 112. Sensing element 122 may occupy a majority of the surface area of bladder sensor 114 that contacts bladder wall 112. While sensing element 122 is rectangular in shape, the strain gauge may be formed of any symmetric or asymmetrical shape. In the example of FIGS. 12 and 13, sensor 114 may have a patch-like shape, and may have a length of approximately 2 to 15 mm, a width of approximately 2 to 10 mm, and a thickness of approximately 2 to 10 mm.

Fixation holes 128, 130, 132 and 134 each contain a pair of passages through housing 116. Each pair of passages is located near a corner of housing 116. A surgeon may pass a suture through these holes to attach housing 116 to bladder 14 in a desired location of bladder wall 112. While fixation holes 128, 130, 132 and 134 each contain two holes, other embodiments may include more or less holes in housing 116. For example, each corner of housing 116 may only contain one hole. Suture would then pass through the hole and around the outside of housing 116. As a further example, each corner may contain three holes for further securing housing 116 to bladder wall 112.

Other fixation methods to secure bladder sensor 114 to bladder wall 112 may include other structures different than sutures. For example, each corner of housing 116 may contain a barbed needle or helical screw that ejects from housing 116 into bladder wall 112. The barbed needles may secure sensor 114 to bladder 14 without lengthy attachment procedures. Also, surgical adhesives may be used as an alternative, or in addition to, mechanical fasteners such as sutures, needles or screws.

Figure 14:
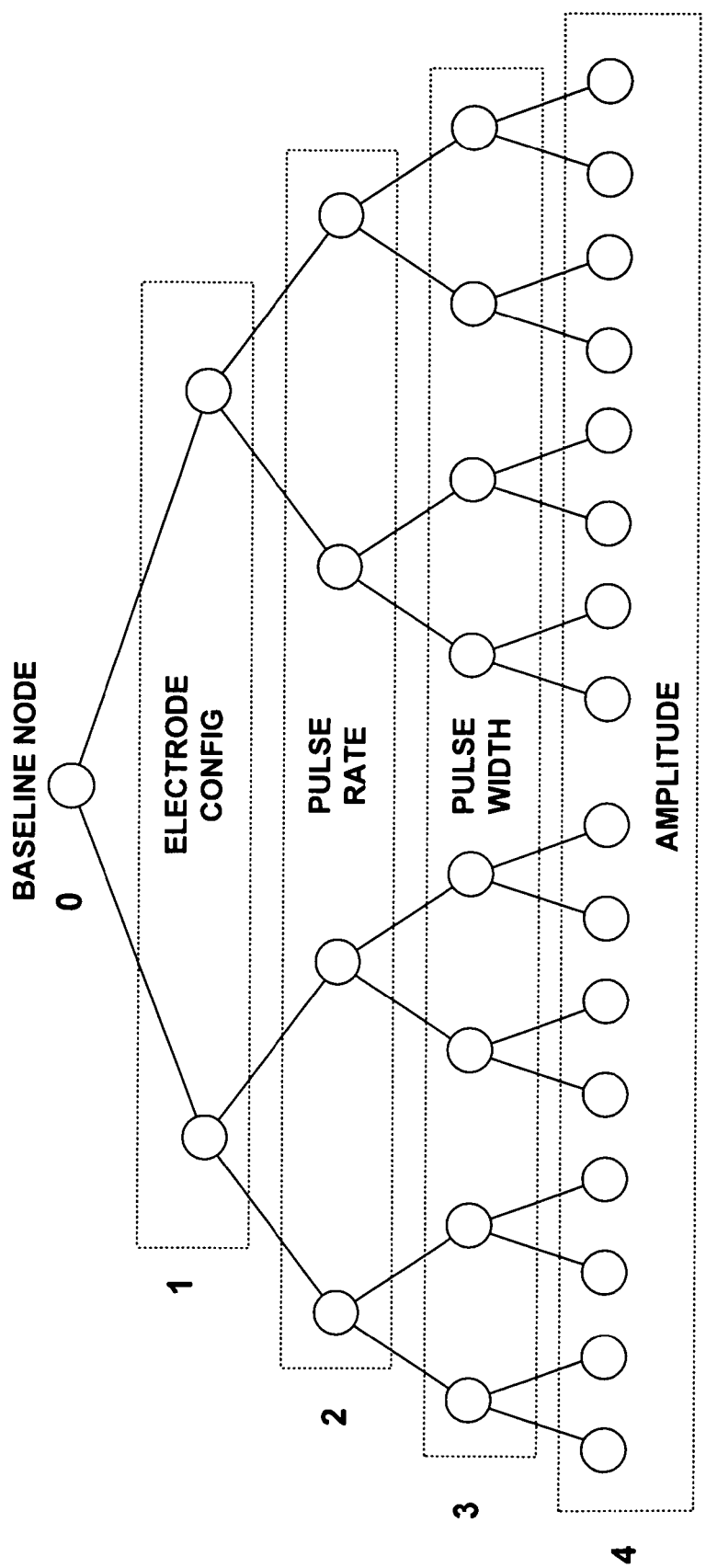
FIG. 14 is a diagram of a therapeutic tree structure for programming parameters associated with stimulation delivered by an implanted stimulator.

FIG. 14 is a diagram of a therapeutic tree structure for programming parameters associated with stimulation delivered by an implanted stimulator. As shown in FIG. 14, the therapeutic tree structure includes a baseline node, representing the baseline condition of the patient without stimulation therapy, at a level 0 of the tree. At level 1, the tree includes two or more nodes specifying parameter sets for stimulation therapy. The parameter sets may specify electrode configurations (including combination and polarity, if applicable), pulse rate, pulse width and voltage or current amplitude.

In the example of FIG. 14, the different nodes in level 1 represent identical values for pulse rate, pulse width and amplitude, but different electrode configurations. The pulse rate, pulse width and amplitude values are initial values that may be predetermined or selected by the clinician. Hence, the different nodes in level 1 represent different electrode configurations. As one example, one node may specify a combination of two electrodes as cathode and anode, while another node specifies the same combination of electrodes, but as anode and cathode. Hence, the level 1 nodes present different electrode configurations and/or polarities.

Each node in level 1 is connected to two or more nodes in level 2. Each node in level 2 has the same electrode configuration as the node to which it is connected above in level 1. In addition, the pulse width and amplitude values for the level 2 nodes may be the same as in level 1. However, in level 2, different nodes connected to the same level 1 node have different pulse rate values. Hence, level 2 represents different pulse rate adjustments to the stimulation program, give the other parameter values defined by the node above.

Each node in level 2 is connected to two or more nodes in level 3. Each node in level 3 has the same electrode configuration and pulse rate as the node to which it is connected above in level 2. In addition, the amplitude values for the level 3 nodes may be the same in level 1. In level 3, however, different nodes connected to the same level 2 node have different pulse width values. Hence, level 3 represents different pulse width adjustments to the stimulation program, given the other parameter values defined by the node above.

Each node in level 3 is connected to two or more nodes in level 4. Each node in level 4 has the same electrode configuration, pulse rate and pulse width as the node to which it is connected above in level 3. However, different nodes connected to the same level 3 node have different amplitude values. Hence, level 4 represents different amplitude adjustments to the stimulation program, given the other parameter values defined by the node above.

The physician, patient, programmer and/or stimulator travel along a path through the therapeutic tree based on efficacy information provided by efficacy feedback from the patient, physician, and/or one or more sensors. For example, the physician or patient may control the path through the tree by entering efficacy information into a programmer, in which case the programmer may map the next node in the tree, either automatically or under user control.

In addition, in some embodiments, the programmer or neurostimulator may define the program path automatically based on efficacy input received from the patient or clinician via the programmer, or information received from one or more sensors. In each case, relative efficacy provided by stimulation parameters associated with the nodes serves to guide the program along the tree to the next node.

In the example of FIG. 14, the order of levels proceeds from electrode combination/polarity at level 1, to pulse rate at level 2, pulse width at level 3, and amplitude at level 4. Hence, the therapy parameters are prioritized such that electrode combination/polarity is used for high-level coarse tuning, as it is perceived as heavily impacting stimulation efficacy, e.g., due to it role in positioning the stimulation relative to a target tissue site.

The other parameters are prioritized in order of impact to provide progressively finer tuning of the stimulation parameter set. For example, after electrode combination/polarity, pulse rate may be viewed as having the next largest impact on efficacy, followed by pulse width and pulse amplitude. The prioritization shown in FIG. 14 is for purposes of example, however, and should not be considered limiting of the invention. Rather, in other embodiments or implementations, the order of parameters among the hierarchy of the therapeutic tree may be subject to variation.

Although each level in the example tree of FIG. 14 represents bifurcated branching from a node above, i.e., from one node to two nodes, each node may branch to two, three, or more nodes in the next level below. In addition, although FIG. 14 shows four levels, not counting the baseline node, additional levels may be added to the tree for additional stimulation parameters or to permit more fine tuning of any of the parameters adjusted in the levels above. Accordingly, the tree in FIG. 4 is provided for purposes of illustration, and may be simpler or more complex for a given implementation.

Figure 15:
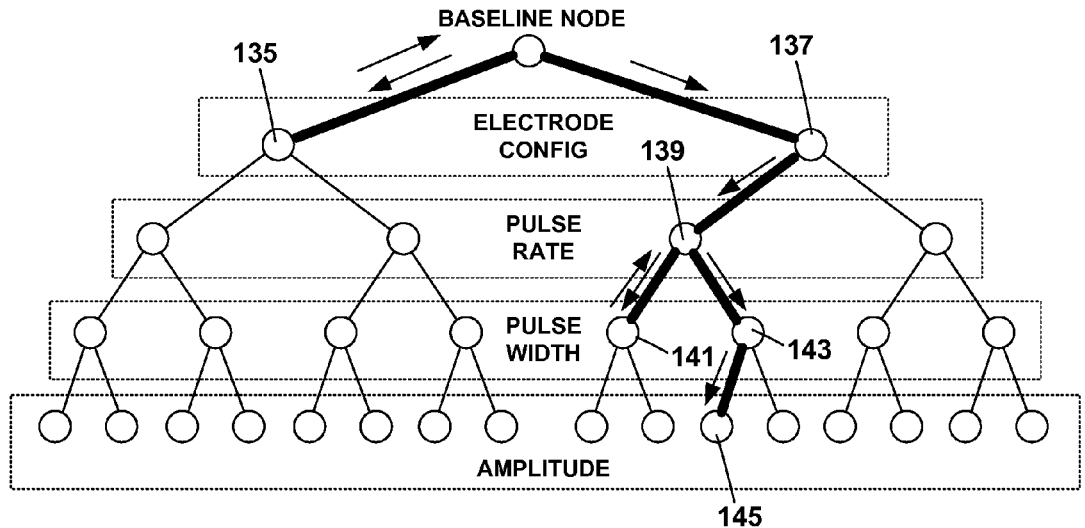
FIG. 15 is a diagram illustrating traversal of the therapeutic tree to define an example program path.

FIG. 15 is a diagram illustrating traversal of the therapeutic tree of FIG. 14 to define an example program path. As shown in FIG. 15, the program path first traverses from the baseline node downward to a first node 135 in level 1, which defines a particular electrode combination and/or polarity. In this example, the efficacy improvement produced by node 135 relative to the patient's baseline condition, i.e., without therapy, is less than a specified threshold level, e.g., 50%. Accordingly, the program path progresses no further down the path connected to node 135, and instead reverses through the baseline node to the second node 137 at level 1. In this case, node 137 presents an efficacy improvement in excess of 50%, and the program path proceeds to the next node 139, which resides in level 2 and specifies a change in pulse rate, while maintaining the electrode configuration and other parameters of node 137.

Node 139 defines stimulation parameters that are found to yield an efficacy improvement in excess of 50%. As a result, the program path continues along a path connected to node 139. In particular, the program path first evaluates parameters associated with node 141 in level 3. Node 141 represents an adjustment to pulse width, while maintaining the electrode configuration and pulse rate specified by node 139. However, the efficacy feedback reveals that node 141 does not achieve an efficacy improvement of greater than 50%. For this reason, the program path returns to node 139 and traverses another branch of node 139 to node 143.

At node 143, the stimulation parameters produce an efficacy improvement in excess of 50% relative to the baseline condition of the patient. In response, the program path proceeds to node 145 in level 4, which represents a change in amplitude but otherwise maintains the parameter values associated with node 143 in level 3. Generally, a 50 percent efficacy improvement relative the baseline patient condition is required to continue along a path extending from a particular node. However, once a program path reaches the bottom of the tree, e.g., level 4, additional program paths may still be created until a higher percent efficacy is reached, e.g., 80%.

Once patient 12 is experiencing an 80 percent efficacy improvement relative to the baseline condition along a given program path, the process may be terminated at the current node in that program path or the process may only proceed to fine tune parameters using lower levels along the same path. As mentioned previously, the 50% and 80% efficacy thresholds are only examples, and the clinician may set them to any percentage of complete efficacy or efficacy improvement, where 100 percent efficacy or efficacy improvement means there are no voiding events during therapy.

Figure 16:
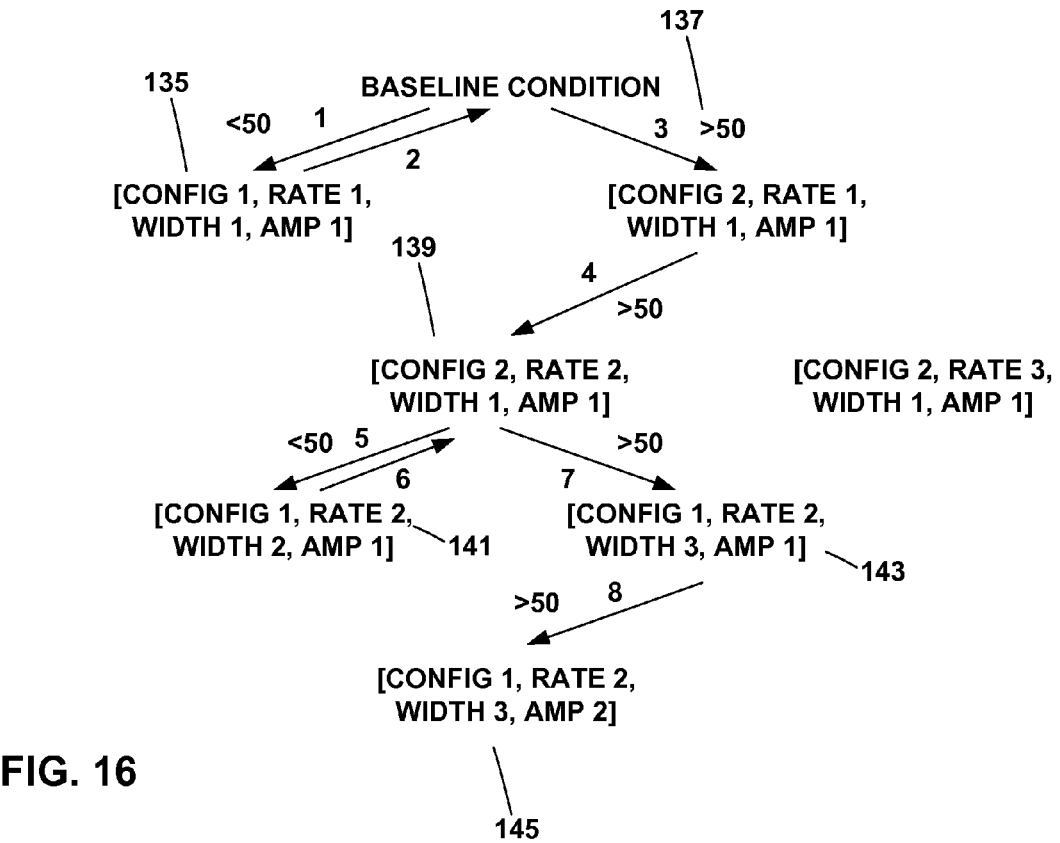
FIG. 16 is a diagram illustrating the program path of FIG. 15 in terms of parameter sets associated with nodes in the program path.

FIG. 16 is a diagram illustrating the program path of FIG. 15 in terms of parameter sets associated with nodes in the program path. In particular, FIG. 16 shows parameter sets corresponding to nodes 135, 137, 139, 141, 143 and 145 of FIG. 15. In addition, FIG. 16 numbers the steps along the program path as steps 1, 2, 3, 4, 5, 6, 7, and 8. As shown, nodes 135 and 137 include similar parameter sets but different electrode configurations. In particular, node 135 specifies [Config 1, Rate 1, Width 1, Amp 1] and node 137 specifies [Config 2, Rate 1, Width 1, Amp 1], where configuration represents electrode combination/polarity, rate represents pulse rate, width presents pulse width and amp represents amplitude. In the next level, FIG. 16 shows node 139 in terms of the parameter set [Config 2, Rate 2, Width 1, Amp 1]. In this case, the electrode configuration, pulse width and amplitude are the same as node 137 above, but Rate 2 is different from Rate 1, representing a pulse rate adjustment.

Figure 17:
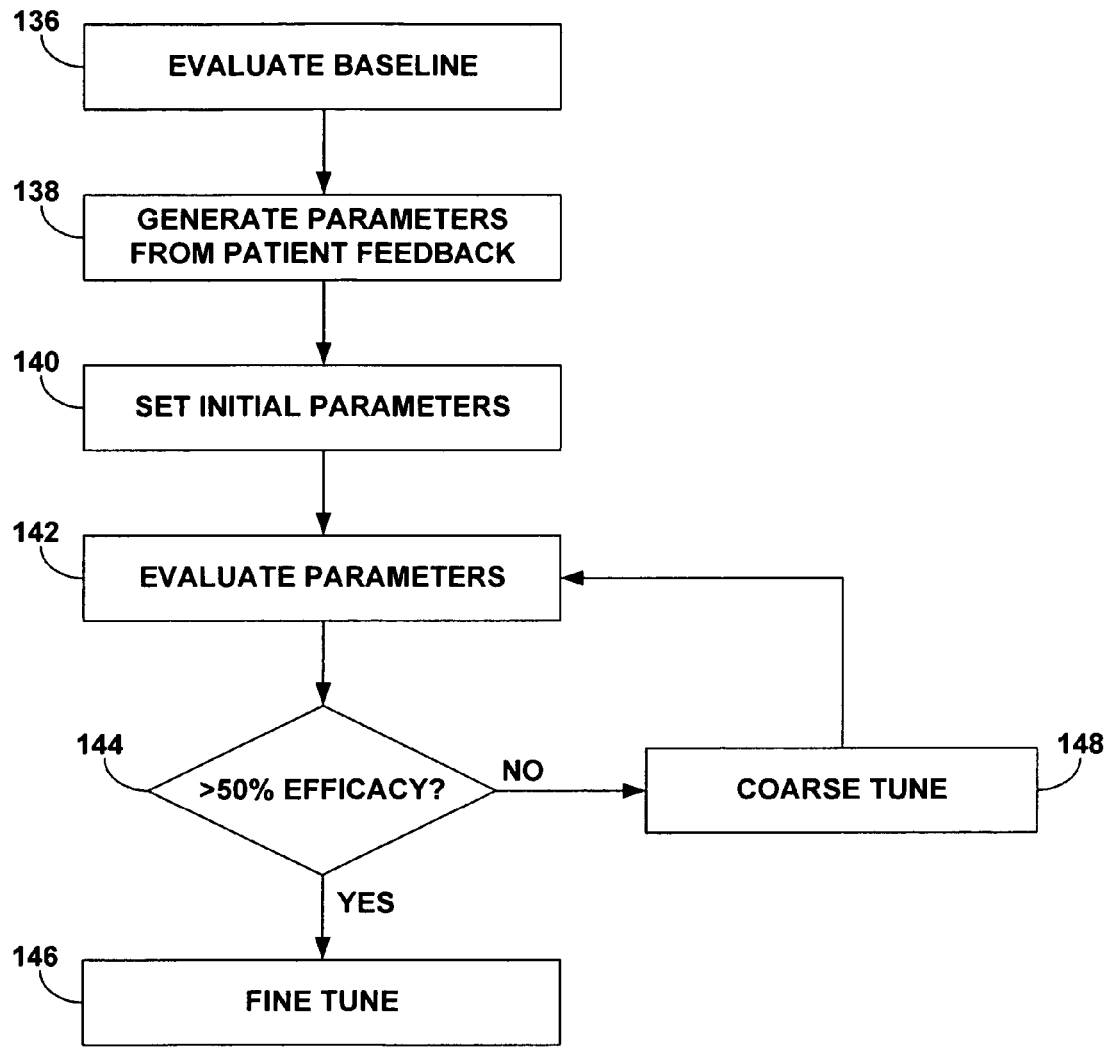
FIG. 17 is a flow chart illustrating a technique for programming the implanted stimulator.

FIG. 17 is a flow chart illustrating a technique for programming the implanted stimulator. As shown in FIG. 17, the clinician aids patient 12 in initially finding a program path to deliver stimulation therapy. First, patient 12 evaluates the baseline, which means providing feedback to criteria from external programmer 24 describing the initial condition of the patient without stimulation (136), e.g., the severity of incontinence for the patient before stimulation is applied. From the baseline information, external programmer 24 generates initial parameters to begin stimulation therapy (138). The initial parameters may be specified or approved by the clinician. At this point in the process, the therapeutic tree has not yet been used. The clinician uses external programmer 24 to begin initial stimulation (140) to evaluate nodes in the therapeutic tree.

The clinician helps patient 12 to evaluate the stimulation therapy from the initial parameters (142). In some cases, patient 12 may have to evaluate the therapy over a long period of time, such as 24 hours or more. If the feedback from patient 12 indicates that the initial stimulation therapy is greater than 50 percent efficacious (144) relative to the baseline condition, external programmer 24 moves directly into fine tuning, i.e., by moving to a lower level of the therapeutic tree (146). If the therapy is less than 50 percent effective (144), external programmer 24 moves to gross or coarse tune by moving to another node of the first level of the therapeutic tree to more coarsely change the stimulation therapy (148). Then, patient 12 evaluates the new parameters of the gross tune (142). Fine tuning further follows the therapeutic tree and is described in FIG. 18.

While patient 12 is described herein as providing feedback, other embodiments may include system 28 or 32 automatically detecting therapy efficacy and changing the program path according to the therapeutic tree. For example, system 28 or 32 may detect efficacy based on sensor signals representing physiological conditions indicative of efficacy. In other embodiments, the efficacy threshold may not be 50 percent. The efficacy threshold may be lower or higher than 50 percent, as determined by the clinician or patient 12.

Figure 18:
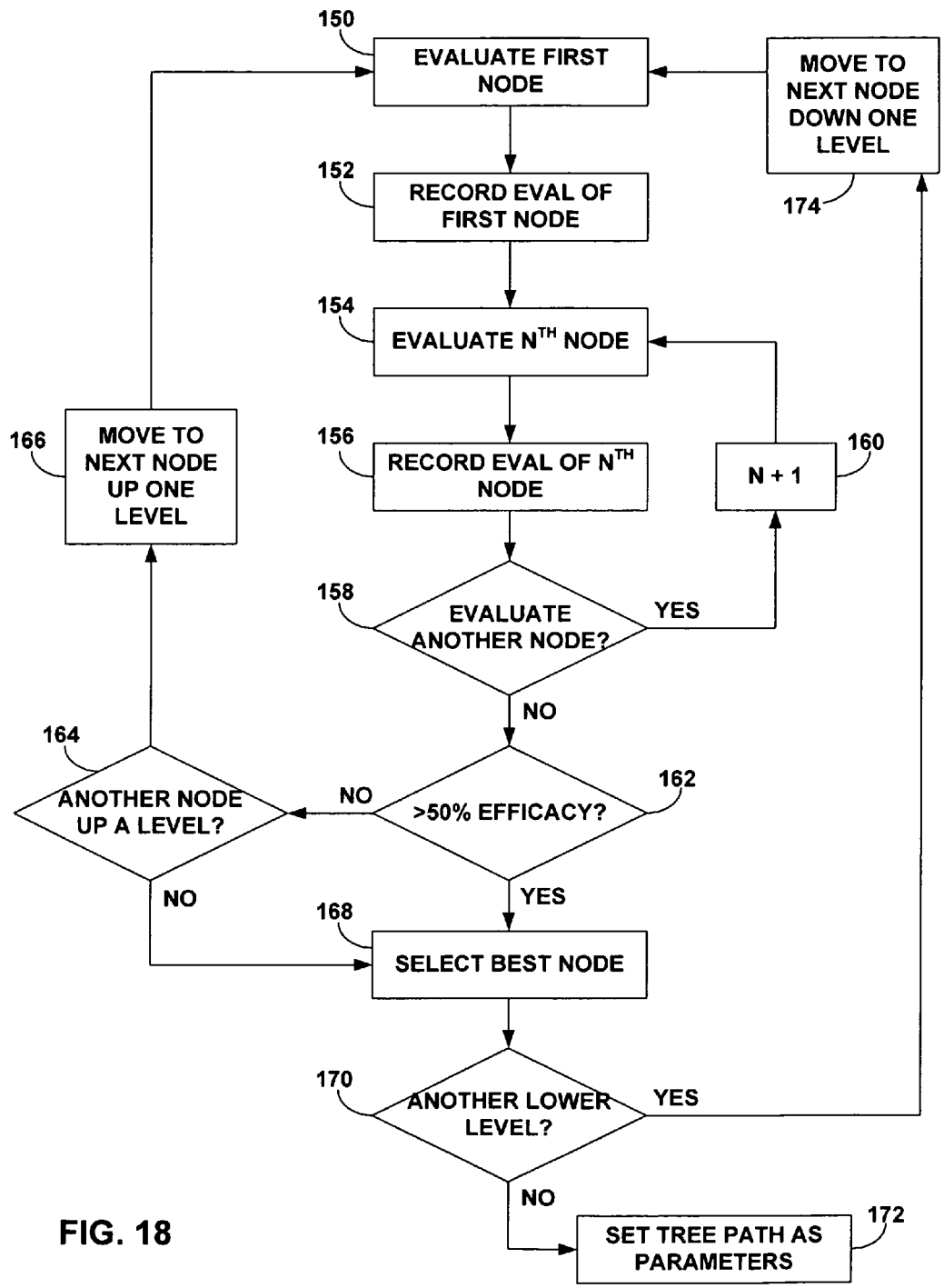
FIG. 18 is a flow chart illustrating a technique for fine tuning the programming of the implanted stimulator.

FIG. 18 is a flow chart illustrating a technique for fine tuning the programming of the implanted stimulator. As shown in FIG. 18, the therapeutic tree is used to fine tune stimulation therapy by creating a program path to best treat patient 12. The patient first evaluates the first node of the second level (150). Patient 12 records the evaluation of the first node using programmer 24 (152). Next, patient 12 evaluates the Nth node (154) and the patient records the evaluation of the Nth node (156). If there is another node of the second level to evaluate (158), programmer 24 adds 1 to the Nth node (160) and patient 12 evaluates the N+1 node (154). If there is no other node to evaluate, programmer 24 determines if any of the evaluated nodes reached greater than 50 percent efficacy (162).

If no nodes of the second level provides greater than 50 percent efficacy, external programmer 24 checks if there is a level up one level from the current position on the therapeutic tree (164). If there is another level, programmer 24 moves up one level (166) and patient 12 evaluates another node of that upper level (150). If there is no level higher up the tree (164) or one of the evaluated nodes is greater than 50 percent efficacious (152), external programmer 24 selects the best node (168).

If there is a lower lever on the therapeutic tree (170), programmer 24 moves to the lower level, i.e. the third level in this example (174), and another node of the third level is evaluated (150). If there are no lower levels on the therapeutic tree to evaluate (170), programmer 24 sets the current program path as the nodes, or stimulation parameters, to deliver stimulation therapy to patient 12.

FIG. 18 shows patient 12 providing feedback to external programmer 24 to create a program path in the therapeutic tree, but system 28 or 32 may automatically create a program path based upon the detected efficacy from the stimulation therapy. In either case, creating a program path may take only minutes, or creating the program path may take days or weeks. As mentioned above, the efficacy threshold of 50 percent may be greater or lower in other embodiments.

Figure 19:
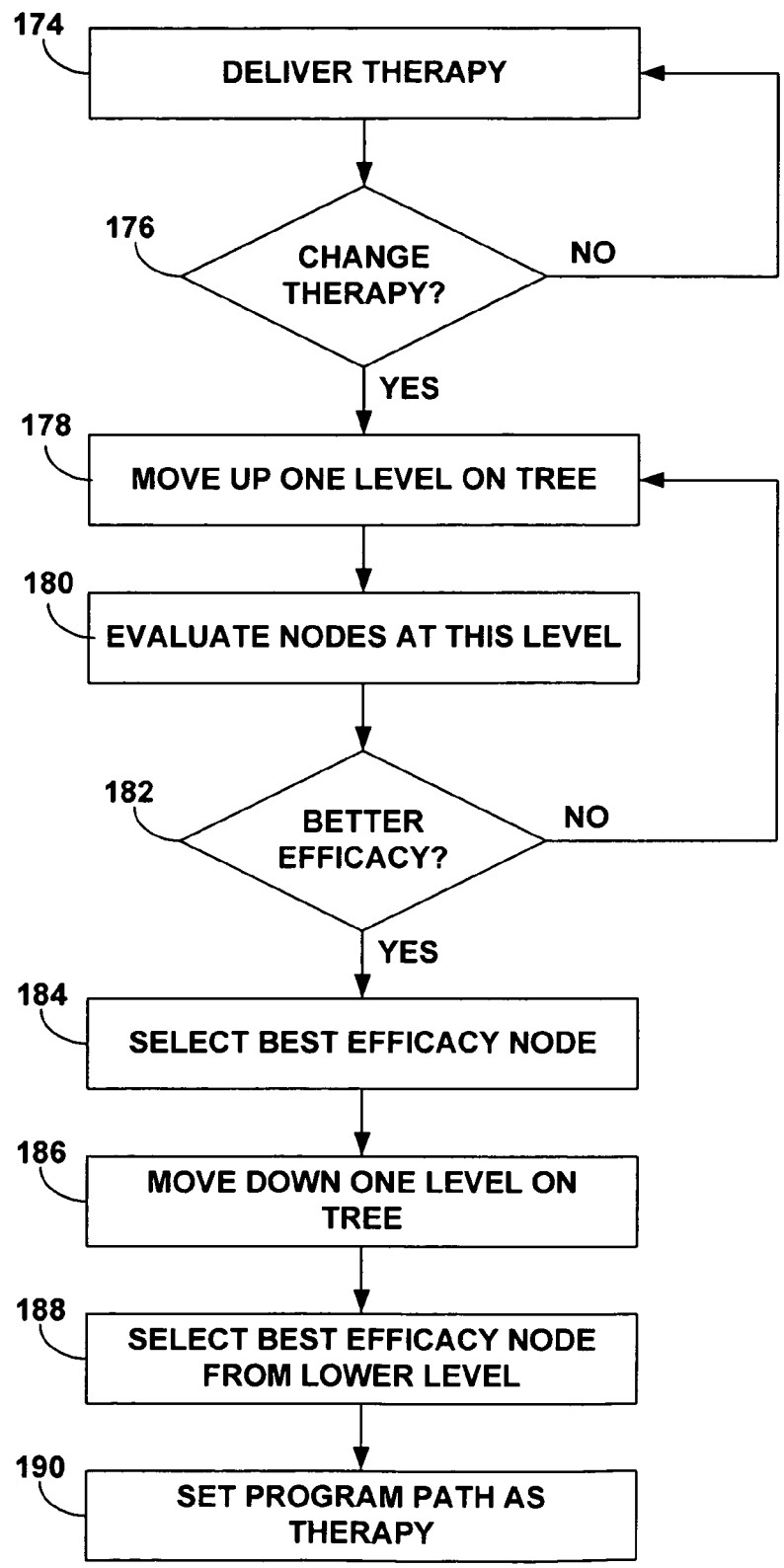
FIG. 19 is a flow chart illustrating a technique for fine tuning stimulation therapy during therapy delivery.

FIG. 19 is a flow chart illustrating a technique for fine tuning stimulation therapy during therapy delivery. As shown in FIG. 19, the program path that defines stimulation therapy may be modified during therapy. Neurostimulator 20 delivers therapy to patient 12 (174), and if there is no indication to change therapy (176), therapy continues unchanged. The indication to change therapy may be from neurostimulator 20, patient 12, or the clinician. If therapy should change (176), programmer 24 moves up one level on the therapeutic tree (178). Patient 12 evaluates the nodes at this level (180) such that programmer 24 may determine if any nodes provide better efficacy (182). If no nodes provide better efficacy, programmer 24 moves up one more level on the therapeutic tree (178).

If at least one evaluated node provides better efficacy (182), programmer 24 selects the best efficacy node based upon patient 12 feedback (184). Programmer 24 moves down one level on the therapeutic tree from the selected node (186) and programmer 24 selects the best efficacy based upon the additional patient 12 feedback (188). Programmer 24 sets the program path as the stimulation parameters for therapy and delivers the stimulation to patient 12.

While patient 12 may manually provide feedback to external programmer 24, sensors 30 or 38 may automatically transmit efficacy information to the programmer. Therefore, programmer 24 may use the therapeutic tree to automatically adjust stimulation therapy according to detected voiding events. During automatic control, patient 12 or the clinician may override the program path selected by programmer 24 or neurostimulator 20, depending on which device is controlling the therapy.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure Many embodiments of the invention have been described. Various modifications may be made without departing from the scope of the claims. For example, although the invention has been generally described in conjunction with implantable neurostimulation devices, a bladder sensor may also be used with other implantable medical devices, such as electrical muscle stimulation devices, functional electrical stimulation (FES) devices, and implantable drug delivery devices, each of which may be configured to treat incontinence or other conditions or disorders. These and other embodiments are within the scope of the following claims.

The invention claimed is:

1. A method for providing electrical stimulation therapy, the method comprising:
    defining a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters;
    defining a program path through the tree along a series of the interconnected nodes, wherein defining the program path comprises:
        selecting one of the nodes in the program path, wherein the selected node is associated with a selected level;
        delivering stimulation therapy to a patient based on a first set of parameters defined by the selected node, the first set of parameters comprising a first stimulation parameter and a second stimulation parameter different than the first stimulation parameter;
        determining an efficacy of stimulation therapy based on the first set of parameters;
        modifying the first stimulation parameter of the first set if the efficacy of stimulation therapy based on the first set of parameters is less than or equal to a threshold level, wherein the first stimulation parameter is associated with the selected level or a higher level of the tree structure relative to the selected level; and
    modifying the second stimulation parameter of the first set if the efficacy of stimulation therapy based on the first set of parameters is greater than the threshold level, wherein the second stimulation parameter is associated with a lower level of the tree structure relative to the selected level.

2. The method of claim 1, wherein the stimulation therapy is configured to treat urinary incontinence.

3. The method of claim 1, further comprising specifying which stimulation parameters are adjusted at which levels of the tree based on user input.

4. The method of claim 1, further comprising receiving efficacy input indicating the efficacy of the delivered stimulation therapy.

5. The method of claim 4, further comprising receiving the efficacy input from a user.

6. The method of claim 4, wherein receiving the efficacy input includes determining the efficacy input based on physiological information obtained via a sensor.

7. The method of claim 1, wherein the tree comprises at least four levels.

8. The method of claim 7, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

9. The method of claim 1, wherein the stimulation parameters include stimulation electrode configuration, stimulation pulse rate, stimulation pulse width, and stimulation pulse amplitude.

10. The method of claim 1, further comprising defining the tree within an external programmer associated with an implantable electrical stimulator.

11. A system for providing electrical stimulation therapy, the system comprising:
    a memory defining a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters; and
    a processor that defines a program path through the tree along a series of the interconnected nodes, wherein the processor defines the program path by at least
        selecting one of the nodes in the program path, wherein the selected node is associated with a selected level;
        controlling delivery of stimulation therapy to a patient based on a first set of parameters defined by the selected node, the first set of parameters comprising a first stimulation parameter and a second stimulation parameter different than the first stimulation parameter;
        determining an efficacy of stimulation therapy based on the first set of parameters; and
        modifying the first stimulation parameter of the first set if the efficacy of stimulation therapy based on the first set of parameters is less than or equal to a threshold level, wherein the first stimulation parameter is associated with the selected level or a higher level of the tree structure relative to the selected level; and
        modifying the second stimulation parameter of the first set if the efficacy of stimulation therapy based on the first set of parameters is greater than the threshold level, wherein the second stimulation parameter is associated with a lower level of the tree structure relative to the selected level.

12. The system of claim 11, wherein the stimulation therapy is configured to treat urinary incontinence.

13. The system of claim 11, wherein the processor specifies which stimulation parameters are adjusted at which levels of the tree based on user input.

14. The system of claim 11, wherein the processor receives efficacy input indicating the efficacy of the delivered stimulation therapy.

15. The system of claim 14, wherein the processor receives the efficacy input from a user.

16. The system of claim 14, wherein the processor receives the efficacy input by at least determining the efficacy input based on physiological information obtained via a sensor.

17. The system of claim 11, wherein the tree comprises at least four levels.

18. The system of claim 17, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

19. The system of claim 11, wherein the stimulation parameters include stimulation electrode configuration, stimulation pulse rate, stimulation pulse width, and stimulation pulse amplitude.

20. The system of claim 11, wherein the processor resides within an external programmer associated with an implantable electrical stimulator.

21. A computer-readable medium comprising instructions to cause a processor to:
    define a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters;

define a program path through the tree along a series of the interconnected nodes;

select one of the nodes in the program path, wherein the selected node is associated with a selected level;

control delivery of stimulation therapy to a patient based on a first set of parameters defined by the selected node, the first set of parameters comprising a first stimulation parameter and a second stimulation parameter;

determine an efficacy of the stimulation therapy based on the first set of parameters;

modify the first stimulation parameter of the first set if the efficacy of the stimulation therapy based on the first set of parameters is less than or equal to a threshold level, wherein the first stimulation parameter is associated with the selected level or a higher level of the tree structure relative to the selected level; and modify the second stimulation parameter of the first set if the efficacy of the stimulation therapy based on the first set of parameters is greater than the threshold level, wherein the second stimulation parameter is associated with a lower level of the tree structure relative to the selected level.

22. The computer-readable medium of claim 21, wherein the stimulation therapy is configured to treat urinary incontinence.

23. The computer-readable medium of claim 21, wherein the instructions cause the processor to specify which stimulation parameters are adjusted at which levels of the tree based on user input.

24. The computer-readable medium of claim 21, wherein the instructions cause the processor to receive efficacy input indicating the efficacy of the delivered stimulation therapy.

25. The computer-readable medium of claim 24, wherein the instructions cause the processor to receive the efficacy input from a user.

26. The computer-readable medium of claim 24, wherein the instructions cause the processor to receive the efficacy input includes determining the efficacy input based on physiological information obtained via a sensor.

27. The computer-readable medium of claim 21, wherein the tree comprises at least four levels.

28. The computer-readable medium of claim 27, wherein a first, top level of the tree specifies an adjustment to stimulation electrode configuration, a second level specifies an adjustment to stimulation pulse rate, a third level specifies an adjustment to stimulation pulse width, and a fourth, bottom level specifies an adjustment to stimulation pulse amplitude.

29. The computer-readable medium of claim 21, wherein the stimulation parameters include stimulation electrode configuration, stimulation pulse rate, stimulation pulse width, and stimulation pulse amplitude.

30. The computer-readable medium of claim 21, wherein the instructions cause the processor to define the tree within an external programmer associated with an implantable electrical stimulator.

31. A system for providing electrical stimulation therapy, the system comprising:

means for defining a tree structure having a plurality of levels and a plurality of nodes in each of the levels, wherein each of the nodes is interconnected with at least one node above and at least two nodes below in the tree, each node defines a set of electrical stimulation parameters, the nodes in each level specify an adjustment to at least one of the parameters, and the node in different levels specify the adjustment to different parameters;

means for defining a program path through the tree along a series of the interconnected nodes, wherein the means for defining comprises:

means for selecting one of the nodes in the program path, wherein the selected node is associated with a selected level;

means for delivering stimulation therapy to a patient based on a first set of parameters defined by the selected node, the first set of parameters comprising a first stimulation parameter and a second stimulation parameter different than the first stimulation parameter;

means for determining an efficacy of stimulation therapy based on the first set of parameters;

means for modifying the first stimulation parameter of the first set if the efficacy of stimulation therapy based on the first set of parameters is less than or equal to a threshold level, wherein the first stimulation parameter is associated with the selected level or a higher level of the tree structure relative to the selected level; and means for modifying the second stimulation parameter of the first set if the efficacy of stimulation therapy based on the first set of parameters is greater than the threshold level, wherein the second stimulation parameter is associated with a lower level of the tree structure relative to the selected level.

32. The method of claim 1, wherein the threshold level comprises a percent increase of efficacy relative to a baseline condition of the patient and determining the efficacy comprises determining an increase in efficacy.

33. The system of claim 11, wherein the threshold level comprises a percent increase of efficacy relative to a baseline condition of the patient and the processor determines the efficacy of stimulation therapy by at least determining an increase in efficacy.

* * * * *